(12) United States Patent
Beier

(10) Patent No.: US 10,815,527 B2
(45) Date of Patent: Oct. 27, 2020

(54) DETERMINATION OF PLATELET-MIRNAS IN ALZHEIMER'S DISEASE

(71) Applicant: Hummingbird Diagnostics GmbH, Heidelberg (DE)

(72) Inventor: Markus Beier, Weinheim (DE)

(73) Assignee: HUMMINGBIRD DIAGNOSTICS GMBH, Heidelberg (DE)

( * ) Notice: Subject to any disclaimer, the term of this patent is extended or adjusted under 35 U.S.C. 154(b) by 0 days.

(21) Appl. No.: 15/105,766

(22) PCT Filed: Dec. 19, 2014

(86) PCT No.: PCT/EP2014/078638
§ 371 (c)(1),
(2) Date: Jun. 17, 2016

(87) PCT Pub. No.: WO2015/091902
PCT Pub. Date: Jun. 25, 2015

(65) Prior Publication Data
US 2017/0002411 A1 Jan. 5, 2017

(30) Foreign Application Priority Data
Dec. 19, 2013 (EP) .................................... 13198619

(51) Int. Cl.
*C12Q 1/68* (2018.01)
*C12Q 1/6883* (2018.01)

(52) U.S. Cl.
CPC ..... *C12Q 1/6883* (2013.01); *C12Q 2600/158* (2013.01); *C12Q 2600/178* (2013.01)

(58) Field of Classification Search
CPC .................................................. C12Q 1/6883
See application file for complete search history.

(56) References Cited

FOREIGN PATENT DOCUMENTS

| WO | WO-2009036236 A1 * | 3/2009 | ........... C12N 15/113 |
| WO | WO-2011080316 A1 * | 7/2011 | ........... C12Q 1/6886 |
| WO | WO-2013024469 A1 * | 2/2013 | ........... C12Q 1/6883 |

OTHER PUBLICATIONS

Ple et al. PLoS ONE, 2012, 7(12), E50746.*
Leidinger et al. Genome Biology 2013, 14R78, pp. 1-16 (Year: 2013).*
TruSeq Small RNA Sample Preparation Guide, Illumina, Nov. 2010, pp. 1-35 (Year: 2010).*
Customer Service Letter, Illumina, Oct. 2011, pp. 1-15 (Year: 2011).*
Schipper et al. Gene Regulation and Systems Biology 2007, 1, 263-274 (Year: 2007).*
Dangwal et al. Hamostaseologie, 2013; 33:17-20 (Year: 2013).*
Ex parte Klimberg et al. Appeal 2014-009712, U.S. Appl. No. 11/332,702, mailed Nov. 21, 2016 (Year: 2016).*
Nagalla et al. Blood, 2011, 117, 5189-5197 (Year: 2011).*
Leidinger et al. Genome Biology 2013, 14R78, pp. 1-16 and supporting information thereof (Year: 2013).*
Yiannopoulou et al. Ther. Adv. Neurol. Disord. 2013, 6, 19-33 (Year: 2013).*
Sheinerman et al. Aging, 2012, 4, 590-605 (Year: 2012).*

* cited by examiner

*Primary Examiner* — Matthew P Coughlin
(74) *Attorney, Agent, or Firm* — Wenderoth, Lind & Ponack, L.L.P.

(57) ABSTRACT

The present invention relates to methods, kits and uses for determining platelet-miRNAs in a from a platelet-comprising fraction derived from a whole blood sample from a subject affected or suspected to be affected by Alzheimer's Disease.

12 Claims, 5 Drawing Sheets

Specification includes a Sequence Listing.

Figure 1:

| SEQ ID NO: | miRNA | Sequence |
|---|---|---|
| 1 | hsa-miR-30c-5p | uguaaacauccuacacucucagc |
| 2 | hsa-miR-425-5p | aaugacacgaucacucccguuga |
| 3 | hsa-miR-151a-3p | cuagacugaagcuccuugagg |
| 4 | hsa-miR-30d-5p | uguaaacauccccgacuggaag |
| 5 | hsa-miR-186-5p | caaagaauucuccuuuugggcu |
| 6 | hsa-miR-125a-5p | ucccugagacccuuuaaccuguga |
| 7 | hsa-miR-191-5p | caacggaaucccaaaagcagcug |
| 8 | hsa-let-7f-5p | ugagguaguagauuguauaguu |
| 9 | hsa-miR-185-5p | uggagagaaaggcaguuccuga |
| 10 | hsa-miR-103a-3p | agcagcauuguacagggcauga |
| 11 | hsa-let-7a-5p | ugagguaguagguuguauaguu |
| 12 | hsa-miR-107 | agcagcauuguacagggcauca |
| 13 | hsa-miR-148b-3p | ucagugcaucacagaacuuugu |
| 14 | hsa-miR-98 | ugagguaguaaguuguauuguu |
| 15 | hsa-let-7g-5p | ugagguaguaguuuguacaguu |
| 16 | hsa-miR-15a-5p | uagcagcacauaaugguuugug |
| 17 | hsa-miR-451a | aaaccguuaccauuacugaguu |
| 18 | hsa-miR-221-3p | agcuacauugucugcuggguuuc |
| 19 | hsa-miR-21-5p | uagcuuaucagacugauguuga |
| 20 | hsa-miR-126-5p | cauuauuacuuuugguacgcg |

Figure 2 :

| SEQ ID NO: | miRNA | Healthy Control, median g1 | Alzheimer median g2 | Fold Change (g1 / g2) | ttest adjpval | limma adjpval | AUC | wmw adjpval |
|---|---|---|---|---|---|---|---|---|
| 1 | hsa-miR-30c-5p | 2226 | 5055 | 2.27 | 7.72E-04 | 7.30E-04 | 0.22 | 1.32E-03 |
| 2 | hsa-miR-425-5p | 3756 | 7571 | 2.02 | 9.91E-05 | 2.84E-06 | 0.17 | 1.75E-04 |
| 3 | hsa-miR-151a-3p | 2693 | 5302 | 1.97 | 1.65E-07 | 1.33E-07 | 0.09 | 4.60E-06 |
| 4 | hsa-miR-30d-5p | 9762 | 18120 | 1.86 | 1.92E-10 | 3.82E-08 | 0.07 | 2.73E-06 |
| 5 | hsa-miR-186-5p | 3474 | 6160 | 1.77 | 3.00E-04 | 6.87E-06 | 0.17 | 1.75E-04 |
| 6 | hsa-miR-125a-5p | 508 | 890 | 1.75 | 5.06E-02 | 2.80E-02 | 0.30 | 3.04E-02 |
| 7 | hsa-miR-191-5p | 103136 | 179039 | 1.74 | 2.06E-01 | 1.65E-01 | 0.39 | 1.67E-01 |
| 8 | hsa-let-7f-5p | 18120 | 11686 | 0.64 | 2.78E-07 | 5.47E-07 | 0.92 | 2.73E-06 |
| 9 | hsa-miR-185-5p | 549 | 347 | 0.63 | 2.73E-02 | 7.66E-02 | 0.66 | 7.56E-02 |
| 10 | hsa-miR-103a-3p | 7015 | 4396 | 0.63 | 6.53E-05 | 1.66E-03 | 0.76 | 2.79E-03 |
| 11 | hsa-let-7a-5p | 19907 | 12395 | 0.62 | 3.15E-06 | 1.38E-06 | 0.90 | 5.47E-06 |
| 12 | hsa-miR-107 | 6607 | 3756 | 0.57 | 3.92E-05 | 1.10E-03 | 0.78 | 1.77E-03 |
| 13 | hsa-miR-148b-3p | 418 | 218 | 0.52 | 4.64E-03 | 2.37E-03 | 0.75 | 3.90E-03 |
| 14 | hsa-miR-98 | 298 | 153 | 0.51 | 8.12E-05 | 3.37E-05 | 0.83 | 1.75E-04 |
| 15 | hsa-let-7g-5p | 4396 | 2226 | 0.51 | 1.36E-05 | 6.87E-06 | 0.86 | 4.62E-05 |
| 16 | hsa-miR-15a-5p | 1959 | 860 | 0.44 | 9.21E-06 | 8.19E-06 | 0.86 | 4.62E-05 |
| 17 | hsa-miR-451a | 179039 | 75965 | 0.42 | 1.71E-01 | 2.22E-01 | 0.65 | 1.05E-01 |
| 18 | hsa-miR-221-3p | 193 | 80 | 0.41 | 1.02E-02 | 2.06E-02 | 0.72 | 1.53E-02 |
| 19 | hsa-miR-21-5p | 469 | 193 | 0.41 | 2.38E-02 | 2.06E-02 | 0.69 | 3.36E-02 |
| 20 | hsa-miR-126-5p | 525 | 183 | 0.35 | 1.88E-02 | 1.51E-02 | 0.71 | 2.20E-02 |

Figure 3

| A | B | C | D | E |
|---|---|---|---|---|
| Seq ID NO: | Stem-Loop Reverse Primer | Forward Primer | Reverse Primer | Dual-Labeled Probe |
| 1 | X-GCTGAGAG | Y-TGTAAACATCCTACACT | Z | 56-FAM-P-GCTGAGAG-3IABLFQ |
| 2 | X-TCAACGGG | Y-AATGACACGATCACTCC | Z | 56-FAM-P-TCAACGGG-3IABLFQ |
| 3 | X-CCTCAAGG | Y-CTAGACTGAAGCTCC | Z | 56-FAM-P-CCTCAAGG-3IABLFQ |
| 4 | X-CTTCCAGT | Y-TGTAAACATCCCCGAC | Z | 56-FAM-P-CTTCCAGT-3IABLFQ |
| 5 | X-AGCCCAAA | Y-CAAAGAATTCTCCTTT | Z | 56-FAM-P-AGCCCAAA-3IABLFQ |
| 6 | X-TCACAGGT | Y-TCCCTGAGACCCTTTAAC | Z | 56-FAM-P-TCACAGGT-3IABLFQ |
| 7 | X-CAGCTGCT | Y-CAACGGAATCCCAAAAG | Z | 56-FAM-P-CAGCTGCT-3IABLFQ |
| 8 | X-AACTATAC | Y-TGAGGTAGTAGATTGT | Z | 56-FAM-P-AACTATAC-3IABLFQ |
| 9 | X-TCAGGAAC | Y-TGGAGAGAAAGGCAGT | Z | 56-FAM-P-TCAGGAAC-3IABLFQ |
| 10 | X-TCATAGCC | Y-AGCAGCATTGTACAGGG | Z | 56-FAM-P-TCATAGCC-3IABLFQ |
| 11 | X-AACTATAC | Y-TGAGGTAGTAGGTTGT | Z | 56-FAM-P-AACTATAC-3IABLFQ |
| 12 | X-TGATAGCC | Y-AGCAGCATTGTACAGGG | Z | 56-FAM-P-TGATAGCC-3IABLFQ |
| 13 | X-ACAAAGTT | Y-TCAGTGCATCACAGAA | Z | 56-FAM-P-ACAAAGTT-3IABLFQ |
| 14 | X-AACAATAC | Y-TGAGGTAGTAAGTTGT | Z | 56-FAM-P-AACAATAC-3IABLFQ |
| 15 | X-AACTGTAC | Y-TGAGGTAGTAGTTTGT | Z | 56-FAM-P-AACTGTAC-3IABLFQ |
| 16 | X-CACAAACC | Y-TAGCAGCACATAATGG | Z | 56-FAM-P-CACAAACC-3IABLFQ |
| 17 | X-AACTCAGT | Y-AAACCGTTACCATTAC | Z | 56-FAM-P-AACTCAGT-3IABLFQ |
| 18 | X-GAAACCCA | Y-AGCTACATTGTCTGCTG | Z | 56-FAM-P-GAAACCCA-3IABLFQ |
| 19 | X-TCAACATC | Y-TAGCTTATCAGACTGA | Z | 56-FAM-P-TCAACATC-3IABLFQ |
| 20 | X-CGCGTACC | Y-TAGCTTATCAGACTGA | Z | 56-FAM-P-CGCGTACC-3IABLFQ | with X =5'-CTCAACTGGTGTCGTGGAGTCGGCAATTCAGTTGAG with Y =5'-ACACTCCAGCTGGG with Z =5'-CTCAACTGGTGTCGTGGAGT with P =5'-TTCAGTTGAG with 56-FAM =5' 6-FAM (Fluorescein)

with 3IABLFQ=Iowa black fluorescein quencher

Figure 4

| Seq ID NO: | Forward Primer | Reverse Primer |
|---|---|---|
| 1 | CAGTGTAAACATCCTACACTCTC | TCCAGTTTTTTTTTTTTTTTGCTGA |
| 2 | GCAGAATGACACGATCACTC | GGTCCAGTTTTTTTTTTTTTTTCAAC |
| 3 | GCTAGACTGAAGCTCCTTG | GTCCAGTTTTTTTTTTTTTTTCCTCA |
| 4 | AGTGTAAACATCCCCGACT | CCAGTTTTTTTTTTTTTTTCTTCCAGT |
| 5 | CAGCAAAGAATTCTCCTTTTGG | GGTCCAGTTTTTTTTTTTTTTTAGC |
| 6 | CCCTGAGACCCTTTAACCT | GTCCAGTTTTTTTTTTTTTTTCACAG |
| 7 | CAACGGAATCCCAAAAGC | AGTTTTTTTTTTTTTTTCAGCTGCT |
| 8 | CGCAGTGAGGTAGTAGATTG | GGTCCAGTTTTTTTTTTTTTTTAACTATAC |
| 9 | GTGGAGAGAAAGGCAGTTC | GTCCAGTTTTTTTTTTTTTTTCAGGA |
| 10 | GCAGAGCAGCATTGTACAG | GGTCCAGTTTTTTTTTTTTTTTCATAG |
| 11 | GCAGTGAGGTAGTAGGTTGT | GGTCCAGTTTTTTTTTTTTTTTAACTATAC |
| 12 | GCAGAGCAGCATTGTACAG | GGTCCAGTTTTTTTTTTTTTTTGATAG |
| 13 | AGTCAGTGCATCACAGAAC | GGTCCAGTTTTTTTTTTTTTTTACAAAG |
| 14 | CGCAGTGAGGTAGTAAGTTGT | AGGTCCAGTTTTTTTTTTTTTTTAACA |
| 15 | CGCAGTGAGGTAGTAGTTTG | CAGGTCCAGTTTTTTTTTTTTTTTAAC |
| 16 | CAGTAGCAGCACATAATGGT | GGTCCAGTTTTTTTTTTTTTTTCACA |
| 17 | CAGAAACCGTTACCATTACTGA | GGTCCAGTTTTTTTTTTTTTTTAACTCA |
| 18 | CAGAGCTACATTGTCTGCTG | CAGTTTTTTTTTTTTTTGAAACCCA |
| 19 | GCAGTAGCTTATCAGACTGATG | GGTCCAGTTTTTTTTTTTTTTTCAAC |
| 20 | CGCAGCATTATTACTTTTGGT | CCAGTTTTTTTTTTTTTTTCGCGTA |

Figure 5

| DNA-Fragment add to 3'-end of miRNA | Analysis Technique | Reference |
|---|---|---|
| dC utilizing T4 RNA ligase | microarray | PMID:17105992, Wang, H., et.al., RNA. 151-159 (2007) |
| (bio-dATP)n or (bio-dCTP)n or (bio-dGATP)n or (bio-dAUTP)n with n=1 to 12 utilizing Klenow-Fragment of DNA polymerase I | microarray | PMID:1878666, Vorwerk, S. et al. N. Biotechnol. 25, 142-9 (2008). |
| adding of a complex DNA-tag by ligation | microarray | PMID:21813625, Wyman S.K. et.al., Genome Res. 2011, 21(9):1450-61. |
| TGGAATTCTCGGGTGCCAAGG | Next Generation Sequencing | Illumina, www.illumina.com |
| 5' P-UCGUAUGCCGUCUUCUGCUUGUidT | Next Generation Sequencing | Illumina, www.illumina.com |
| AMP-5'p-5'p-CTGTAGGCACCATCAATdi-deoxyC | Next Generation Sequencing | Illumina, www.illumina.com |
| AMP-5'p-5'p-ATCTCGTATGCCGTCTTCTGCTTGdi-deoxyC | Next Generation Sequencing | Illumina, www.illumina.com |

Figure 6

| A | B | C | D | E |
|---|---|---|---|---|
| 3' RNA Adapter | 5' RNA Adapter | RT Primer | Small RNA PCR Primer 1 | Small RNA PCR Primer 2 |
| P-UCGUAUGCCGUCUUCUGCUUGUidT | GUUCAGAGUUCUACAGUCCGACGAUC | CAAGCAGAAGACGGCATACGA | CAAGCAGAAGACGGCATACGA | AATGATACGGCGACCACCGACAGGTTCAGAGTTCTACAGTCCGA |
| 5' /5rApp/ATCTCGTATGCCGTCTTCTGCTTG/3ddC/ | GUUCAGAGUUCUACAGUCCGACGAUC | CAAGCAGAAGACGGCATACGA | CAAGCAGAAGACGGCATACGA | AATGATACGGCGACCACCGACAGGTTCAGAGTTCTACAGTCCGA |
| 5' TGGAATTCTCGGGTGCCAAGG | 5' GUUCAGAGUUCUACAGUCCGACGAUC | 5' GCCTTGGCACCCGAGAATTCCA | CAAGCAGAAGACGGCATACGAGATCGTGATGTGACTGGAGTTCCTTGGCACCCGAGAATTCCA | AATGATACGGCGACCACCGAGATCTACACGTTCAGAGTTCTACAGTCCGA | with : (A) 3' RNA Adapter = DNA fragment added to 3'end of miRNA via ligation reaction (B) 5' RNA Adapter = DNA fragment added to 5'end of miRNA via ligation reaction (C) RT Primer = primer for reverse-transcribing said RNA-DNA hybrid to cDNA (D) Small RNA PCR Primer 1 = universal forward primer for amplifying the cDNAs (E) Small RNA PCR Primer 2 = universal reverse primer for amplifying the cDNAs

__DETERMINATION OF PLATELET-MIRNAS IN ALZHEIMER'S DISEASE__

RELATED APPLICATIONS

This application is a national stage filing under 35 U.S.C. § 371 of international application number PCT/EP2014/078638, filed Dec. 19, 2014, which claims the benefit of European application number 13198619.2, filed Dec. 19, 2013, each of which is herein incorporated by reference in its entirety.

TECHNICAL FIELD OF THE INVENTION

The present invention relates to methods, use and kits for the determination of platelet-miRNAs in Alzheimer's Disease (AD).

BACKGROUND OF THE INVENTION

Today, biomarkers play a key role in early diagnosis, risk stratification, and therapeutic management of various diseases. MicroRNAs (miRNAs) are a new class of biomarkers. They represent a group of small noncoding RNAs that regulate gene expression at the posttranslational level by degrading or blocking translation of messenger RNA (mRNA) targets. So far, miRNAs have been extensively studied in tissue material where it was found that miRNAs are expressed in a highly tissue-specific manner. Since recently it is known that miRNAs are not only present in tissues but also in body fluid samples, including blood. Nevertheless, the mechanism why miRNAs are found in blood, especially in the cellular blood fraction (blood cells of subfractions thereof) or in the extra-cellular fraction (serum/plasma), or their function in these blood fractions is not understood yet.

The inventors of the present invention assessed for the first time the expression of platelet-miRNAs in Alzheimer's Disease (AD) in a platelet-comprising fraction derived from a whole blood sample. They surprisingly found that especially the platelet-miRNAs are significantly dysregulated in whole blood samples of subjects affected with AD. Therefore, the inventors of the present invention followed different approaches to determine expression profiles of platelet-miRNA in platelet-comprising fractions of whole blood samples.

In a first approach the inventors determined expression profiles of platelet-miRNAs in AD directly from whole blood samples without prior depletion of removal of white blood cells and/or red blood cells, hence in front of a background of white blood cells and/or red blood cells (or without isolation of platelets). This is surprising since the RNA-content of the anucleated platelets is approximately 10.000 times lower when compared to the RNA-content of the nucleated white blood cells, with which the platelets are mixed in the whole blood sample collected in said whole blood collection tubes. Surprisingly, the expression of the platelet-miRNAs can be determined directly from total RNA isolated from the mixture of platelets, white blood cells and red blood cells present in the whole blood collected in whole blood collection tubes (preferably collected in Paxgene-like tubes, more preferably collected in PAXgene™ Blood RNA tubes) without the need for prior depletion or removal of the white blood cells and/or the red blood cells. Hence the expression of the platelet-miRNAs can be determined in front of a background of white blood cells and/or red blood cells, without the need to isolate (or enrich) the platelets or the platelet fraction from the whole blood sample before. This is of advantage to applications, especially diagnostic applications, where the determination of said platelet-miRNAs can be directly determined from a whole blood sample without the need for additional sample processing steps (e.g. removal or depletion of the red blood cells and/or white blood cell fractions, or isolation of the platelet fraction). This results in easier, quicker, cheaper preanalytic processing of such samples, which is especially valuable for competitive diagnostic applications. The inventors of the present invention further surprisingly found that platelet-miRNAs that are determined from total RNA isolated from whole blood samples without prior depletion and/or removal of white blood cells and/or red blood cells (or in front of a background of white blood cells and/or red blood cells; or without prior isolation of the platelet fraction), may be employed as biomarkers for non-invasive diagnosis of AD, or for non-invasive diagnosis of a platelet-related (platelet-activated) component of AD. Furthermore, it was found that platelet-miRNAs that are determined from total RNA isolated from whole blood samples without prior depletion or removal of white blood cells and/or red blood cells (or in front of a background of white blood cells and/or red blood cells; or without prior isolation of the platelet fraction), may be employed as biomarkers for determining the platelet-activity in AD and/or for monitoring the efficacy of anti-platelet therapy in AD. Therefore, the inventors of the present invention found that the whole blood collection tubes, preferably Paxgene-like tubes, more preferably PAXgene™ Blood RNA tubes, are suitable or useful for determination of expression profiles of platelet-miRNAs without prior depletion or removal of white blood cells and/or red blood cells (or in front of a background of white blood cells and/or red blood cells; or without prior isolation of the platelet fraction) and that such expression profiles may be used in a method for non-invasive diagnosis of AD, or for non-invasive diagnosis of platelet-related (platelet-activated) components of AD and for determining platelet-activity in AD or for monitoring the efficacy of anti-platelet therapy in AD.

In a second approach the inventors determined expression profiles of platelet-miRNAs in AD with prior depletion or removal of the white blood cells and/or the red blood cells, or with isolation of the platelet-fraction. Hence, by depleting or removing of the white blood cells and/or the red blood cells from the whole blood sample or by isolating the platelets, a platelet-comprising fraction (e.g. platelet-rich-plasma, platelet concentrate) is obtained, from which the expression profile of said set of at least one platelet-miRNA was determined. Hence the expression of the platelet-miRNAs can be determined without a background of white blood cells and/or red blood cells, allowing to determine platelets that are expressed at lower levels which would not possible to determine in front of a background of white blood cells and/or red blood cells. This allows for a clear separation of (biomarker) information originating from the platelet-comprising fraction on the one side and from the white blood cells or the red blood cells on the other side. This increased sensitivity for determining platelet-miRNAs may be of advantage to especially diagnostic applications, where the determination of certain platelet-miRNAs, especially those expressed at low levels, is required with high sensitivity, e.g. in the diagnosis of AD. Said expression profiles that were determined from total RNA isolated from whole blood samples with prior depletion and/or prior removal of white blood cells and/or red blood cells (or with prior isolation of the platelet-comprising fraction) may be employed as biomarkers for non-invasive diagnosis of AD, for non-invasive diagnosis of platelet-related (platelet-activated) components of AD, or for determining the platelet-activity in AD or for monitoring the efficacy of anti-platelet therapy in AD.

SUMMARY OF THE INVENTION

In a first aspect, the invention provides for a method for diagnosing a platelet-related or platelet-activated component of Alzheimer's Disease by determining an expression profile of a set comprising at least one platelet-miRNA from a whole blood sample of a subject, wherein the expression profile is determined from a platelet-comprising fraction derived from said whole blood sample.

In a second aspect, the invention provides for a method for diagnosing Alzheimer's Disease by determining an expression profile of a set comprising at least one platelet-miRNA from a whole blood sample of a subject, wherein the expression profile is determined from a platelet-comprising fraction derived from said whole blood sample.

In a third aspect, the invention provides for a method for monitoring the progression of Alzheimer's Disease in a subject by determining an expression profile of a set comprising at least one platelet-miRNA from a whole blood sample of a subject, wherein the expression profile is determined from a platelet-comprising fraction derived from said whole blood sample.

In a fourth aspect, the invention provides for a method for determining the platelet activity in a subject affected by Alzheimer's Disease by determining an expression profile of a set comprising at least one platelet-miRNA from a whole blood sample of a subject wherein the expression profile is determined from a platelet-comprising fraction derived from said whole blood sample.

In a fifth aspect, the invention provides for a method for monitoring the efficacy of an anti-platelet therapy in a subject affected by Alzheimer's Disease by determining an expression profile of a set comprising at least one platelet-miRNA from a whole blood sample of a subject, wherein the expression profile is determined from a platelet-comprising fraction derived from said whole blood sample.

In a sixth aspect, the invention provides for kit for use in the method according to any of the first, second, third, fourth or fifth aspect of the invention, comprising:
  a) means for determining an expression profile of a set comprising at least one platelet-miRNA
  b) a reference derived from at least one reference expression profile
  c) optionally a data carrier
  d) optionally means for deriving a platelet-comprising fraction from a whole blood sample
  e) optionally a whole blood collection tube
  wherein the expression profile and the reference expression profile are obtained from said set of at least one platelet-miRNAs selected from the group consisting SEQ ID NO: 1 to 20 and wherein the expression profile and the reference expression profile are determined from a platelet-comprising fraction derived from a whole blood sample.

This summary of the invention does not necessarily describe all features of the invention.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

To practice the present invention, unless otherwise indicated, conventional methods of chemistry, biochemistry, and recombinant DNA techniques are employed which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used in this specification and in the appended claims, the singular forms "a", "an", and "the" include plural referents, unless the content clearly dictates otherwise. For example, the term "a test compound" also includes "test compounds".

The terms "microRNA" or "miRNA" refer to single-stranded RNA molecules of at least 10 nucleotides and of not more than 35 nucleotides covalently linked together. The miRNAs regulate gene expression and are encoded by genes from whose DNA they are transcribed, but miRNAs are not translated into protein (i.e. miRNAs are non-coding RNAs). The terms "microRNA*" or "miRNA*" refer to miRNA molecules derived from the passenger strand upon processing. In the context of the present invention, the terms "miRNA" and "miRNA*" are interchangeable used. The miRBase (www.mirbase.org) is a well established repository and searchable database of published miRNA sequences and annotation. Because of the conservation of miRNAs among species, for example between humans and other mammals, e.g. animals such as mice, monkey or rat, a human miRNA may also be suitable for detecting the respective miRNA orthologue(s) in another species, e.g. in another mammal, e.g. in an animal such as mouse or rat or vice versa.

The term "platelet" as used in the context of the present invention refers to the smallest type of blood cells, also known as "thrombocytes", which are released into the blood stream from bone marrow megakaryocytes. Platelets play a crucial role in haemostasis and thrombosis. Platelets do not contain a nucleus, therefore missing substantial parts of the microRNA machinery components required for transcription and nuclear processing. Platelets comprise approximately 10.000 times less RNA when compared to nucleated cells (e.g. white blood cells). Platelets contain miRNAs (PMID 21415270, 22371016, 23323973), but it is not yet completely understood where these originate from and how these interact in translational control or repression of platelet mRNAs.

The term "platelet-miRNA(s)" as used in the context of the present invention refers to a miRNA(s) that is (are) expressed in platelets (thrombocytes). This does not necessarily mean that these platelet-miRNAs are exclusively expressed in platelets and not in any other blood cells, in other cells, in other body fluids or in tissue. Currently, there are approximately 400 miRNA described to be expressed in platelets. The platelet-miRNAs in AD according to the present invention are selected from the group consisting of SEQ ID NO: 1 to SEQ ID NO: 20 and are listed in FIG. 1. According to the present invention the expression level of said platelet-miRNAs selected from the group consisting of SEQ ID NO: 1 to SEQ ID NO: 20 are in a range that allows for direct determination from a whole blood sample of a subject affected by AD or suspected to be affected by AD without the need for additional sample processing steps (e.g. removal or depletion of the red blood cells and/or white blood cell fractions, or isolation of the platelet fraction), which is of advantage to commercial applications, especially in the field of diagnostics. Hence, the platelet-miRNAs selected from the group consisting of SEQ ID NO: 1 to SEQ ID NO: 20 can be determined directly from a whole blood sample without prior depletion or removal of the white blood cells and/or the red blood cells. This allows to make the biomarker information contained in the platelet-miRNAs directly available without prior removal or depletion of the red blood cells and/or white blood cells. Furthermore, besides the criteria of being reproducibly expressed in platelets and showing sufficient expression level, the inventors of the present invention applied further criteria based on expression data for selection of said 20 platelet-miRNAs with SEQ ID NO: 1 to SEQ ID NO: 20 from the approximately 400 miRNAs that are described to be expressed in platelets. The inventors investigated Alzheimer's Disease patients and healthy controls and selected said 20 platelet-miRNAs with SEQ ID NO: 1 to SEQ ID NO: 20 from the expression data (e.g. see FIG. 2) by applying a 1.5-fold threshold for differential expression between the disease subjects (subjects affected by AD or suspected to be affected by AD) and the healthy control subjects. Alternatively, the expression profile of said set of at least one platelet miRNA selected from the group consisting of SEQ ID NO: 1 to 20 may be determined after isolation of the platelet-comprising fraction, e.g by isolating the platelets from the whole blood sample or by depletion or removal of the white blood cells and/or the red blood cells from the whole blood sample.

The term "whole blood sample", as used in the context of the present invention, refers to a blood sample originating from a subject containing all blood fractions, including both the cellular (red blood cells, white blood cells, platelets) and the extra-cellar blood fractions (serum, plasma). The "whole blood sample" may be derived by removing blood from a subject by conventional blood collecting techniques, but may also be provided by using previously isolated and/or stored blood samples. Preferably, the whole blood sample from a subject (e.g. human or animal) has a volume of between 0.1 and 40 ml, more preferably of between 0.5 and 20 ml, more preferably between 1 and 15 ml and most preferably between 2 and 10 ml, i.e. 0.1, 0.2, 0.3, 0.4, 0.5, 0.6, 0.7, 0.8, 0.9, 1, 2, 2.5, 3, 4, 5, 6, 7, 8, 9, 10, 51, 12, 13, 14, 15, 16, 17, 18, 19, 20, 21, 22, 23, 24, 25, 26, 27, 28, 29, 30, 31, 32, 33, 34, 35, 36, 37, 38, 39 or 40 ml.

The term "platelet-comprising fraction" as used in the context of the present invention refers to a fraction of a whole blood sample that comprises platelets. Hence, that platelet-comprising fraction may contain—besides platelets—also white blood cells and/or red blood cells or alternatively said platelet-comprising fraction comprises substantially (only) platelets. An example for the first case is a mixture of platelets, white blood cells and red blood cells which is present in a whole blood sample. An example for the second case is platelet-rich-plasma or platelet concentrate, which are derived from a whole blood sample from which the white blood cells and the red blood cells were removed. A platelet-comprising fraction is a (useful) source from which an expression profile of a set comprising at least one platelet-miRNA can be determined with or without prior depletion of removal of white blood cells and/or red blood cells (preferably not in front or in front of a background of white blood cells and/or red blood cells or preferably with or without isolation of platelets).

The term "whole blood collection tube" as used in the context of the present invention relates to blood collection tube, that is used for collection of whole blood samples, preferably a whole blood collection tube according to the present invention is a Paxgene-like tube, a PAXgene™ Blood RNA tube, a Tempus Blood RNA tube, an EDTA-tube, a Na-citrate tube or a ACD-tube (Acid citrate dextrose). Preferably, when the whole blood sample is collected, the RNA-fraction, —especially the miRNA fraction—may be protected/guarded against degradation. For this purpose special whole blood collection tubes (e.g. PAXgene™ Blood RNA tubes from Preanalytix, Tempus™ Blood RNA tubes from Applied Biosystems) or additives (e.g. RNAlater™ from Ambion, RNAsin® from Promega, RNA Retain® from Asuragen, catrimox-14 or tetradecyltrimethyl-ammonium oxalate or derivatives thereof), that stabilize the RNA fraction and/or the miRNA fraction, may be employed.

The term "Paxgene-like tube" as used in the context of the present invention relates to blood collection tubes, which are suited or used for collection of whole blood samples, which contain additives for stabilization of RNA and which are suited for expression analyses of the intracellular RNA and/or intracellular miRNAs and/or platelet-miRNAs. Preferably, herein additives for stabilization of RNA are employed, including, but are not limited to, RNAlater™, RNAsin®, RNA Retain® catrimox-14 or tetradecyltrimethylammonium oxalate or derivatives thereof. It is particularly preferred that "Paxgene-like tubes" are "PAXgene™ Blood RNA tubes", which are suited for collection of whole blood samples and which contain additives for cell lysis and stabilization of intracellular RNA and which are suited for expression analyses of RNAs and/or miRNAs and/or platelet-miRNAs. Preferably, herein additives for cell lysis and stabilization of intracellular RNA include, but are not limited to, catrimox-14 or tetradecyltrimethylammonium oxalate or derivatives thereof. PAXgene™ Blood RNA tubes are currently marketed by PreAnalytix (www.preanalytix.com). Further details on the PAXgene™ tubes (manuals, application notes etc.), its technology and how to use these can be found at the websites of Preanalytix (www.preanalytix.com/product-catalog/blood/), Qiagen (www.qiagen.com/products/catalog/sample-technologies/rna-sample-technologies/) or Becton Dickinson (www.bd.com/vacutainer/products/molecular/). Further details regarding the PAXgene™ technology, especially. regarding said additives for cell lysis and stabilization of intracellular RNA are detailed in U.S. Pat. No. 6,602,718, U.S. Pat. No. 6,617,170, U.S. Pat. No. 6,821,789, U.S. Pat. No. 6,681,213, U.S. Pat. No. 7,270,953, U.S. Pat. No. 7,682,790, WO02/00599, WO94/18156, U.S. Pat. No. 5,985,572, U.S. Pat. No. 5,010,183, which are all incorporated here by reference in their entirety. It is understood that any other blood collection tube, which is suited for collection of whole blood samples, which contain additives for stabilization of intracellular RNA (e.g. EDTA-, Na-citrate or ACD-tubes containing addities like RNAlater™, RNAsin®, RNA Retain® catrimox-14 or tetradecyltrimethylammonium oxalate or derivatives thereof) and which are suited for expression analyses of intracellular RNA and/or intracellular miRNAs, and/or platelet-miRNAs, also fall under the term "Paxgene-like tube" as used in the context of the present invention.

The term "total RNA" as used herein relates to the RNA isolated from a platelet-comprising fraction derived from the whole blood sample. The total RNA, comprising the miRNA-fraction or comprising a miRNA-enriched fraction, is obtained by lysis (e.g. Trizol) of the blood cells of the platelet-comprising fraction derived from the whole blood sample, followed by RNA isolation (extraction) e.g. by phenol/chloroform extraction and/or separation based techniques (e.g. glass fibre filter column, silica-membrane column). Examples of kits for RNA isolation and purification include the miRNeasy Kits (Qiagen), PAXgene™ Blood miRNA Kit (Qiagen), mirVana PARIS Kit (Life Technologies), PARIS Kit (Life Technologies), Tempus Spin RNA Isolation Kit (Life Technologies). Preferably, the total RNA according to the present invention contains the miRNA-fraction or contains a miRNA-enriched fraction.

The term "intracellular RNA" as used herein relates to the RNA present in the blood cells (platelets, white blood cells, red blood cells) of a whole blood sample, comprising the miRNA-fraction.

The term "expression profile" as used in the context of the present invention, represents the a measure that correlates with the miRNA expression (level) in a sample. By determining the miRNA expression profile, each miRNA is represented by a numerical value. The higher the value of an individual miRNA, the higher is the expression level of said miRNA, or the lower the value of an individual miRNA, the lower is the expression level of said miRNA. The expression profile may be generated by any convenient means, e.g. nucleic acid hybridization (e.g. to a microarray), nucleic acid amplification (PCR, RT-PCR, qRT-PCR, high-throughput RT-PCR), ELISA for quantitation, next generation sequencing (e.g. ABI SOLID, Illumina Genome Analyzer, Roche/454 GS FLX), flow cytometry (e.g. LUMINEX, Milipore Guava) and the like, that allow the determination of a miRNA expression profile in a subject and comparison between samples. The sample material measured by the aforementioned means is a platelet-comprising fraction derived from the whole blood sample (with or without prior depletion or removal of the white blood cells and/or the red blood cells or with or without isolation of the platelet fraction or not in front or in front of a background of white blood cells and/or red blood cells), comprising said platelet-miRNAs and may be total RNA, labeled total RNA, amplified total RNA, cDNA, labeled cDNA, amplified cDNA, miRNA, labeled miRNA, amplified miRNA or any derivatives that may be generated from the aforementioned RNA/DNA species. The "expression profile", as used herein, relates to a collection of expression (levels) of at least one miRNAs, preferably of least 1, 2, 3, 4, 5, 6, 7, 8, 9, 10, 11, 12, 13, 14, 15, 16, 17, 18, 19, 20 or more miRNAs.

The term "determining an expression profile" as used herein, relates to the determination of the expression profile of set comprising at least one platelet-miRNA, hence from miRNA(s) expressed in platelets, preferably from miRNAs expressed in platelets selected from the group consisting of SEQ ID NO 1 to 20. By doing so, the determination of the expression profile is a measure that directly or indirectly correlates with the levels of platelet-miRNAs present in said platelet-comprising fraction derived from the whole blood sample. Herein, all steps or transformations required to bring the isolated total RNA (comprising the platelet-miRNAs) into a form which allows to determine the expression profile by any convenient means (e.g. nucleic acid hybridisation, nucleic acid amplification, polymerase extension, mass spectroscopy, flow cytometry, sequencing) and which are known to the person skilled in the art, are included, e.g. RNA- or miRNA-isolation, RNA- or miRNA-enrichment, RNA- or miRNA-purification, RNA- or miRNA-labeling, polymerase extension of RNA or miRNA, ligation of RNA or miRNA, reverse-transcription of RNA or miRNA into cDNA, amplification of the cDNA, labelling of cDNA).

The term "nucleic acid hybridization", as used herein, relates to a means for determining an expression profile. The nucleic acid hybridization may be performed using a microarray/biochip or in situ hybridization. For nucleic acid hybridization, for example, the polynucleotides (probes) with complementarity to the corresponding platelet-miRNAs to be detected are e.g. attached to a solid phase to generate a microarray/biochip. Said microarray/biochip is then incubated with a sample containing the platelet-miRNA(s) (or a species that is derived from said platelet-miRNA(s)), which may be labelled or unlabelled. Quantification of the expression level of the miRNAs may then be carried out e.g. by direct read out of said label or by additional manipulations, e.g. by use of an enzymatic reaction. Alternatively, the polynucleotides which are at least partially complementary to miRNAs having SEQ ID NO: 1 to 20 (or a species derived thereof, e.g. a cDNA-species) are contacted with said sample containing said platelet-miRNA(s) (or a species that is derived from said platelet-miRNA(s), e.g. a cDNA-species) in solution to hybridize. Afterwards, the hybridized duplexes are pulled down to the surface and successfully captured miRNAs are quantitatively determined (e.g. FlexmiR-assay, FlexmiR v2 detection assays from Luminex, Fireplex assayfrom Firefly Bioworks).

The term "nucleic acid amplification", as used herein, relates to a means for determining an expression profile. Nucleic acid amplification may be performed using real time polymerase chain reaction (RT-PCR) such as real time quantitative polymerase chain reaction (RT qPCR). The standard real time polymerase chain reaction (RT-PCR) is preferred for the analysis of a single miRNA or a set comprising a low number of miRNAs (e.g. a set of at least 2 to 10 miRNAs), whereas high-throughput RT-PCR technologies (e.g. OpenArray from Applied Biosystems, Smart-PCR from Wafergen, Biomark System from Fluidigm) are also able to measure large sets (e.g a set of 5, 10, 20, 30, 50, 80, 100, 200 or more) to all known miRNAs in a high parallel fashion. The aforesaid real time polymerase chain reaction (RT-PCR) may include the following steps: (i) extracting the total RNA from platelet-comprising fraction derived from the whole blood sample collected in a whole blood collection tube, preferably collected in a Paxgene-like tube, particularly preferably collected in a PAXgene™ Blood RNA tube, obtained from a subject, (ii) obtaining cDNA samples by RNA reverse transcription (RT) reaction using universal or miRNA-specific primers; (iii) optionally pre-amplifying the cDNA of step (ii) via polymerase chain reaction (PCR), (iv) amplifying the optionally pre-amplified cDNA via polymerase chain reaction (PCR), thereby monitoring the amplification through a previously added fluorescent reporter dye (e.g. SYBR Green) or fluorescent reporter probe (e.g. Taqman probe), and (v) detecting the miRNA(s) level in the sample from the monitoring in step (iv). In Step (i) the isolation and/or extraction of RNA may be omitted in cases where the RT-PCR is conducted directly from the miRNA-containing sample. Kits for determining a miRNA expression profile by real time polymerase chain reaction (RT-PCR) are e.g. from Life Technologies, Applied Biosystems, Ambion, Roche, Qiagen, Invitrogen, SABiosciences, Exiqon.

The term "sequencing", as used herein, relates to a means for determining an expression profile, including conventional (Maxam-Gilbert, Sanger) sequencing technology, Pyrosequencing or next generation sequencing technology (e.g. ABI SOLID, Illumina Hiseq, Gnubio, Pacific Biosystems, 454) or any other sequencing technology, capable of determination of the expression profile of set comprising at least one platelet-miRNA.

The term "reference" as used in the context of the present invention refers to a reference to which the expression profile of a test sample of a subject affected by AD or suspected to be affected by AD is compared in the course of non-invasive diagnosis of AD, or in the course of non-invasive diagnosis of a platelet-related (platelet-activated) component of AD or in the course of determining the platelet-activity in AD and/or in the course of monitoring the efficacy of anti-platelet therapy in AD. Herein, both the expression profile of the subject (affected by AD or suspected to be affected by AD) to be tested as well as the reference, are determined from the same platelet-miRNAs and the same sample type (collected and worked up in the same way), preferably they are determined from a platelet-comprising fraction derived from the whole blood sample collected in whole blood collection tubes, preferably collected in Paxgene-like tubes, more preferably collected in PAXgene™ Blood RNA tubes. The reference may be a reference expression profile obtained from determining one or more expression profiles of a set comprising at least one platelet-miRNA from a platelet-comprising fraction derived from the whole blood sample collected in whole blood collection tubes, preferably obtained from a platelet-comprising fraction derived from the whole blood sample collected in Paxgene-like tubes, more preferably collected in PAXgene™ Blood RNA tubes, in one or more reference subjects. Furthermore, the reference may be an algorithm, a mathematical function or a score that was developed from such aforementioned reference expression profiles.

The term "Alzheimer's Disease" (AD), relates to an irreversible, progressive brain disease that slowly destroys memory and thinking skills, and eventually even the ability to carry out the simplest tasks. In most people with Alzheimer's, symptoms first appear after age 60.

Although it is still not known how the Alzheimer's Disease process begins, it seems likely that damage to the brain starts a decade or more before problems become evident. During the preclinical stage of Alzheimer's Disease, people are free of symptoms but toxic changes are taking place in the brain. Alzheimer's Disease can be definitively diagnosed only after death, but doctors now have several methods and tools to help them determine fairly accurately whether a person who is having memory problems has "possible Alzheimer's Disease". Hence, doctors (a) ask questions about overall health, past medical problems, ability to carry out daily activities, and changes in behavior and personality, (b) conduct tests of memory, problem solving, attention, counting, and language, (c) carry out standard medical tests, such as blood and urine tests, to identify other possible causes of the problem, (d) perform brain scans, such as computed tomography (CT) or magnetic resonance imaging (MRI). Still, there is a need for better and earlier diagnosis in AD. Early, accurate diagnosis is beneficial for several reasons. It can tell people whether their symptoms are from Alzheimer's or another cause, such as stroke, tumor, Parkinson's disease, sleep disturbances, side effects of medications, or other conditions that may be treatable and possibly reversible. Beginning treatment early on in the disease process can help preserve function for some time, even though the underlying disease process cannot be changed. In addition, an early diagnosis can provide greater opportunities for people to get involved in clinical trials to actively support AD drug development.

The term "diagnosing" as used in the context of the present invention refers to the process of determining a possible disease (e.g. Alzheimer's Disease) or disorder or a certain component of a disease (e.g. an inflammatory component, a neuroinflammatory component of a disease) and therefore is a process attempting to define the (clinical) condition of a subject. The determination of the expression profile of at least one platelet-miRNA according to the present invention correlates with the (clinical) condition of said subject. Preferably, the diagnosis comprises (i) determining the occurrence/presence of the disease (or of a component of a disease), especially in an (very) early phase of the disease (ii) monitoring the course or progression of the disease, (iii) staging of the disease, (iv) measuring the response of a patient affected with the disease to therapeutic intervention, (v) monitoring the efficacy of a therapeutic intervention and/or (vi) segmentation of a subject suffering from the disease.

The term "platelet-related component of a AD" as used in the context of the present invention refers to an aspect or feature of AD that is platelet-related or related to the function/disfunction of platelets in AD. Preferably, such platelet-related components include, but are not limited to, haemostasis-related, thrombosis-related, immunity-related, or inflammation-related aspects or features of the disease, more preferably the platelet-related component of AD is a neuroinflammatory component of AD.

The term "platelet-activated component of a AD" as used in the context of the present invention refers to an aspect or feature of AD that is platelet-activated or activated due to function/disfunction of platelets in AD. Preferably, such platelet-activated components include, but are not limited to, haemostasis-activated, thrombosis-activated, immunity-activated, or inflammation-activated aspects or features of AD, more preferably the platelet-activated component of a disease is a neuroinflammatory component of AD.

An overview of the platelet-miRNAs well suited in method, use or kit according to the present invention are the platelet-miRNAs with SEQ ID NO: 1 to 20, which are listed in FIG. 1.

An exemplarily approach to determine expression profiles in AD++-of a set comprising at least one platelet-miRNA selected from the group consisting of SEQ ID NO: 1 to 20 from a platelet-comprising fraction derived from the whole blood sample when starting from whole blood collected in a PAXgene™ Blood RNA tube without prior depletion or removal of white blood cells and/or red blood cells (or without prior isolation of the platelet fraction or in front of a background of white blood cells and/or red blood cells) is summarized below:

Step 1: Providing a whole blood sample of a subject: Whole blood is drawn from a subject (affected by AD or suspected to be affected by AD) into a PAXgene™ Blood RNA tube, drawing of 2.5 ml of whole blood into a PAXgene™ Blood RNA tube is sufficient for the downstream analyses. The tube should be carefully inverted to ensure that the reagents contained are thoroughly mixed with the blood. The tube maybe stored before analysis (e.g. at 4° C. for up to 3 days, at −80° C. for up to several months).

Step 2: Isolation of the total RNA from said whole blood sample: The PAXgene™ Blood RNA tube, which was allowed to incubate at room temperature for at least 1 hour, is centrifuged to form a blood cell pellet (comprising white blood cells, red blood cells, platelets) at the bottom of the tube, which is collected, whereas the supernatant is discarded. The total RNA (comprising the miRNA fraction) is isolated from the collected blood cell pellet (comprising white blood cells, red blood cells, platelets) using suitable kits (e.g. miRNeasy kit) and/or purification methods.

Step 3: Determining an expression profile of a set comprising at least one platelet-miRNA from the total RNA isolated: From the total RNA isolated the expression profile of a set of at least one platelet-miRNA selected from the group consisting of SEQ ID NO: 1 to SEQ ID NO: 20 is measured using experimental techniques. These techniques include but are not limited to nucleic acid hybridisation based approaches, nucleic acid amplification methods (PCR, RT-PCR, qPCR), sequencing, next generation sequencing, flow cytometry and/or mass spectroscopy. In a preferred embodiment, it may be required in Step 3 that the total RNA or that individual platelet-miRNAs are reverse-transcribed into cDNA and optionally be amplified before the expression profile is determined.

In order to make use of the determined expression profiles in a method for diagnosing AD and/or for diagnosing of a platelet-related (or platelet-activated) component of AD and/or for monitoring the progression of AD and/or for determining the platelet activity in AD and/or for monitoring the efficacy of an anti-platelet therapy in AD, further steps are performed:

Step 4: Comparing said expression profile to a reference: The expression profile obtained in Step 3) is compared to a reference. The reference may be e.g. a reference expression profile, obtained from determining the expression profile of said at least one platelet-miRNA from a whole blood sample collected in the same type of whole blood collection tube as in Step 1 (here: collected in a PAXgene™ Blood RNA) in one or more reference subjects or the reference may be an algorithm, a mathematical function or a score that was developed from such a reference expression profile.

Step 5: Identifying if said subject is affected by an AD-related condition: The comparison to the reference then allows to identify if said subject is affected or not affected by AD (and/or the platelet-related (or platelet-activated) component of AD and/or the platelet-related disease, such as AD) or alternatively if certain thresholds for monitoring the progression of a platelet-related (platelet-activated) disease, such as AD, and/or if thresholds for determining the platelet activity in AD and/or if thresholds for monitoring the efficacy of an anti-platelet therapy in AD are reached.

Step 6: Optionally administering said affected subject to therapy: Optionally, said subject, that was identified to be affected by AD (and/or was identified to be affected by the platelet-related (or platelet-activated) component of AD) is administered to therapy, e.g. by treating the subject with drugs suited for therapy of AD (and/or drugs suited for said the platelet-related (or platelet-activated) component of AD). Or alternatively subjecting said subject, if certain thresholds for monitoring the progression of AD and/or if thresholds for determining the platelet activity in AD and/or if thresholds for monitoring the efficacy of an anti-platelet therapy in AD are reached, to an altered therapeutic scheme, wherein said altered therapeutic scheme may be an increased or decreased therapeutic scheme with administering appropriate drugs at increased or decreased dosage. Thus, administering said affected subject to therapy may include administration of cholinesterase inhibitors (Aricept, Exelon, Razadyne, Cognex) for early to moderate stages of AD or memantine (Namenda) to treat the cognitive symptoms (memory loss, confusion, and problems with thinking and reasoning) for moderate to severe stages of Alzheimer's disease.

An exemplarily approach to determine expression profiles in AD of a set comprising at least one platelet-miRNA selected from the group consisting of SEQ ID NO: 1 to 20 platelet-comprising fraction derived from the whole blood sample when starting from whole blood collected in an EDTA-tube, with prior depletion or removal of white blood cells and/or red blood cells (or with prior isolation of the platelet fraction or not in front of a background of white blood cells and/or red blood cells) is summarized below:

Step 1: Providing a whole blood sample of a subject: Whole blood is drawn from a subject (affected by AD or suspected to be affected by AD) into a EDTA-tube (Sarstedt, S-Monovette EDTA-$K_2$, 7.5 ml); drawing of 7.5 ml of whole blood into EDTA-tube tube is sufficient for the downstream analyses. The tube should be carefully inverted to ensure that the reagents contained are thoroughly mixed with the blood. The tube should not kept at room temperature for longer than 4 hours before centrifugation.

Step 2: Depletion or removal of the white blood cells and/or the red blood cells: The collected whole blood sample is centrifuged with soft spin (170 g, 15 min) to separate the blood cell fractions. After centrifugation the whole blood sample is separated into Platelet-Rich-Plasma (PRP, top-fraction), buffy coat (white blood cells; middle-fraction, interphase) and red blood cells (bottom fraction). From this the platelet-comprising fraction, namely the Platelet-Rich-Plasma is collected. Optionally, platelet concentrate, as a further platelet-comprising fraction, may be prepared by subjecting the PRP to a second hard spin centrifugation (5000 g, 3 min), where platelets are pelleted out of the plasma to yield platelet-concentrate and platelet-poor-plasma (PPP).

Step 3: Isolation of the total RNA from said platelet-comprising fraction derived from the whole blood sample: After cell lysis the total RNA is isolated from the platelet-comprising fraction obtained in Step 2, namely from Platelet-Rich-Plasma or from platelet concentrate (each of them comprising said platelet-miRNAs) using suitable kits (e.g. miRNeasy kit) and/or purification methods.

Step 4: Determining an expression profile of a set comprising at least one platelet-miRNA from the total RNA isolated: From the total RNA isolated the expression profile of a set of at least one platelet-miRNA, selected from the group consisting of SEQ ID NO: 1 to SEQ ID NO: 20 is measured using experimental techniques. These techniques include but are not limited to nucleic acid hybridisation based approaches, nucleic acid amplification methods (PCR, RT-PCR, qPCR), sequencing, next generation sequencing, flow cytometry and/or mass spectroscopy. In a preferred embodiment, it may be required in Step 4 that the total RNA or that individual platelet-miRNAs are reverse-transcribed into cDNA and optionally are amplified before the expression profile is determined.

In order to make use of the determined expression profiles in a method for diagnosing AD and/or for diagnosing of a platelet-related (or platelet-activated) component of AD and/or for monitoring the progression of AD and/or for determining the platelet activity in AD and/or for monitoring the efficacy of an anti-platelet therapy in AD, further steps are performed:

Step 5: Comparing said expression profile to a reference: The expression profile obtained in Step 3) is compared to a reference. The reference may be e.g. a reference expression profile, obtained from determining the expression profile of said at least one platelet-miRNA from platelet-comprising fraction derived from the whole blood sample collected in the same type of whole blood collection tube as in Step 1 (here: collected in a EDTA-tube; Sarstedt S-Monovette) in one or more reference subjects or the reference may be an algorithm, a mathematical function or a score that was developed from such a reference expression profile.

Step 6: Identifying if said subject is affected by AD related condition: The comparison to the reference then allows to identify if said subject is affected or not affected by AD (and/or the platelet-related (or platelet-activated) component of AD or alternatively if certain thresholds for monitoring the progression of AD, and/or if thresholds for determining the platelet activity in AD and/or if thresholds for monitoring the efficacy of an anti-platelet therapy in AD are reached.

Step 7: Optionally administering said affected subject to therapy: Optionally, said subject, that was identified to be affected by AD and/or a platelet-related (or platelet-activated) component of AD, is administered to therapy, e.g. by treating the subject with drugs suited for therapy of AD (and/or drugs suited for said the platelet-related (or platelet-activated) component of AD). Or alternatively subjecting said subject, if certain thresholds for monitoring the progression of AD and/or if thresholds for determining the platelet activity in AD and/or if thresholds for monitoring the efficacy of an anti-platelet therapy in AD are reached, to an altered therapeutic scheme, wherein said altered therapeutic scheme may be an increased or decreased therapeutic scheme with administering appropriate drugs at increased or decreased dosage.

Thus, administering said affected subject to therapy may include administration of cholinesterase inhibitors (Aricept, Exelon, Razadyne, Cognex) for early to moderate stages of AD or memantine (Namenda) to treat the cognitive symptoms (memory loss, confusion, and problems with thinking and reasoning) for moderate to severe stages of Alzheimer's disease.

In a first aspect, the present invention relates to method for diagnosing a platelet-related (or platelet-activated) component of Alzheimer's Disease by determining an expression profile of a set comprising at least one platelet-miRNA from a whole blood sample of a subject, wherein the expression profile is determined from a platelet-comprising fraction derived from said whole blood sample.

It is preferred that in said method the set comprising at least one platelet-miRNA is selected from the group consisting of SEQ ID NO: 1 to 20.

It is preferred that the platelet-comprising fraction derived from the whole blood sample is obtained with or without prior depletion or removal of the white blood cells and/or the red blood cells. It is further preferred that the platelet-comprising fraction derived from the whole blood sample is obtained with or without prior isolation of the platelets from the whole blood. It is further preferred that the expression profile of set comprising at least one platelet-miRNA is determined in front or not in front of a background of white blood cells and/or red blood cells.

In a preferred embodiment, the platelet-related or platelet-activated component of Alzheimer's Disease to be determined is an inflammatory component of AD, more preferably it is a neuroinflammatory component of AD.

It is preferred that the whole blood sample is collected in a whole blood collection tube, preferably it is collected in a EDTA-, Na-citrate-, ACD- or a Paxgene-like tube, particularly preferred it is collected in a PAXgene™ Blood RNA tube.

In a preferred embodiment, the expression profile is determined directly from a whole blood sample. Hence the mixture of white blood cells, red blood cells and platelets represents the platelet-comprising fraction derived from said whole blood sample. Thus, the expression profile is directly determined from the total RNA isolated from the whole blood sample without prior depletion or removal of the white blood cells and/or the red blood cells or the expression profile is determined directly from the total RNA isolated from the whole blood sample in front of a background of white blood cells and red blood cells or the expression profile is determined directly from the total RNA isolated from the whole blood sample without prior isolation (or extraction) of the platelet fraction. In that respect, the method of the first aspect of the present invention for diagnosing a platelet-related (or platelet-activated) component of Alzheimer's Disease comprises the following steps:

a. Providing a whole blood sample of a subject
  b. Isolation of the total RNA from said whole blood sample
  c. Determining an expression profile of a set comprising at least one platelet-miRNA from the total RNA isolated
  d. Comparing said expression profile to a reference
  e. Identifying if said subject is affected by a platelet-related (or platelet-activated) component of Alzheimer's Disease
  f. Optionally administering said affected subject to therapy (suitable for AD)

In a further preferred embodiment, the expression profile is determined not directly from a whole blood sample, but from a platelet-comprising fraction of said whole blood sample, that is derived from said whole blood sample. Hence from the mixture of white blood cells, red blood cells and platelets the platelet-comprising fraction is prepared by isolation of the platelet fraction or by depletion or removal of the white blood cells and/or the red blood cells from said whole blood sample, hence the expression profile is determined not front of a background of white blood cells and red blood cells. The platelet-comprising fraction may be isolated from said whole blood sample by convenient means (e.g. by centrifugation, size selection) or it may be obtained by depletion or removal of the white blood cells and/or the red blood cells from said whole blood sample using convenient means (e.g. by centrifugation, size selection, differential cell lysis). In that respect, the method of the first aspect of the present invention for diagnosing a platelet-related or platelet-activated component of Alzheimer's Disease comprises the following steps:
  a. Providing a whole blood sample of a subject
  b. Depletion or removal of the white blood cells and/or the red blood cells from the whole blood sample
  c. Isolation of the total RNA from the sample of step b.
  d. Determining an expression profile of a set comprising at least one platelet-miRNA from the total RNA isolated
  e. Comparing said expression profile to a reference
  f. Identifying if said subject is affected by a platelet-related (or platelet-activated) component of Alzheimer's Disease
  g. Optionally administering said affected subject to therapy (suitable for AD)

In a second aspect, the invention relates to a method for diagnosing Alzheimer's Disease by determining an expression profile of a set comprising at least one platelet-miRNA from a whole blood sample of a subject, wherein the expression profile is determined from a platelet-comprising fraction derived from said whole blood sample.

It is preferred that in said method the set comprising at least one platelet-miRNA is selected from the group consisting of SEQ ID NO: 1 to 20.

It is preferred that the platelet-comprising fraction derived from the whole blood sample is obtained with or without prior depletion or removal of the white blood cells and/or the red blood cells. It is further preferred that the platelet-comprising fraction derived from the whole blood sample is obtained with or without prior isolation of the platelets from the whole blood. It is further preferred that the expression profile of set comprising at least one platelet-miRNA is determined in front or not in front of a background of white blood cells and/or red blood cells.

In a preferred embodiment, Alzheimer's Disease may be diagnosed from a platelet-related component of AD, such as an platelet-related inflammatory component of AD, such as an platelet-related neuroinflammatory component of AD which may be determined from an expression profile of a set comprising at least one platelet-miRNA selected from the group comprising SEQ ID NO: 1 to 20.

It is preferred that the whole blood sample is collected in a whole blood collection tube, preferably it is collected in a EDTA-, Na-citrate-, ACD- or a Paxgene-like tube, particularly preferred it is collected in a PAXgene™ Blood RNA tube.

In a preferred embodiment, the expression profile is determined directly from a whole blood sample. Hence the mixture of white blood cells, red blood cells and platelets represents the platelet-comprising fraction derived from said whole blood sample. Thus, the expression profile is directly determined from the total RNA isolated from the whole blood sample without prior depletion or removal of the white blood cells and/or the red blood cells or the expression profile is determined directly from the total RNA isolated from the whole blood sample in front of a background of white blood cells and red blood cells or the expression profile is determined directly from the total RNA isolated from the whole blood sample without prior isolation (or extraction) of the platelet fraction. In that respect, the method of the second aspect of the present invention for diagnosing Alzheimer's Disease comprises the following steps:
  a. Providing a whole blood sample of a subject
  b. Isolation of the total RNA from said whole blood sample
  c. Determining an expression profile of a set comprising at least one platelet-miRNA from the total RNA isolated
  d. Comparing said expression profile to a reference
  e. Identifying if said subject is affected by AD
  f. Optionally administering said affected subject to therapy (suitable for AD)

In a further preferred embodiment, the expression profile is determined not directly from a whole blood sample, but from a platelet-comprising fraction of said whole blood sample, that is derived from said whole blood sample. Hence from the mixture of white blood cells, red blood cells and platelets the platelet-comprising fraction is prepared by isolation of the platelet fraction or by depletion or removal of the white blood cells and/or the red blood cells from said whole blood sample, hence the expression profile is determined not front of a background of white blood cells and red blood cells. The platelet-comprising fraction may be isolated from said whole blood sample by convenient means (e.g. by centrifugation, size selection) or it may be obtained by depletion or removal of the white blood cells and/or the red blood cells from said whole blood sample using convenient means (e.g. by centrifugation, size selection, differential cell lysis) In that respect, the method of the second aspect of the present invention for diagnosing Alzheimer's Disease comprises the following steps:
  a. Providing a whole blood sample of a subject
  b. Depletion or removal of the white blood cells and/or the red blood cells from the whole blood sample
  c. Isolation of the total RNA from sample of step b.
  d. Determining an expression profile of a set comprising at least one platelet-miRNA from the total RNA isolated
  e. Comparing said expression profile to a reference
  f. Identifying if said subject is affected by AD
  g. Optionally administering said affected subject to therapy (suitable for AD)

In a third aspect, the invention relates to a method for monitoring the progression of Alzheimer's Disease in a subject by determining an expression profile of a set comprising at least one platelet-miRNA from a whole blood sample of a subject, wherein the expression profile is determined from a platelet-comprising fraction derived from said whole blood sample.

It is preferred that in said method the set comprising at least one platelet-miRNA is selected from the group consisting of SEQ ID NO: 1 to 20.

It is preferred that the platelet-comprising fraction derived from the whole blood sample is obtained with or without prior depletion or removal of the white blood cells and/or the red blood cells. It is further preferred that the platelet-comprising fraction derived from the whole blood sample is obtained with or without prior isolation of the platelets from the whole blood. It is further preferred that the expression profile of set comprising at least one platelet-miRNA is determined in front or not in front of a background of white blood cells and/or red blood cells.

In a preferred embodiment, the progression of Alzheimer's Disease may be monitored by monitoring the progression of a platelet-related component of AD, such as a platelet-related inflammatory component of AD, such as a platelet-related a neuroinflammatory component of AD which may be monitored from an expression profile of a set comprising at least one platelet-miRNA selected from the group comprising SEQ ID NO: 1 to 20.

It is preferred that the whole blood sample is collected in a whole blood collection tube, preferably it is collected in a EDTA-, Na-citrate-, ACD- or a Paxgene-like tube, particularly preferred it is collected in a PAXgene™ Blood RNA tube.

In a preferred embodiment, the expression profile is determined directly from a whole blood sample. Hence the mixture of white blood cells, red blood cells and platelets represents the platelet-comprising fraction derived from said whole blood sample. Thus, the expression profile is directly determined from the total RNA isolated from the whole blood sample without prior depletion or removal of the white blood cells and/or the red blood cells or the expression profile is determined directly from the total RNA isolated from the whole blood sample in front of a background of white blood cells and red blood cells or the expression profile is determined directly from the total RNA isolated from the whole blood sample without prior isolation (or extraction) of the platelet fraction. In that respect, the method of the third aspect of the present invention for monitoring Alzheimer's Disease comprises the following steps:
 a. Providing a whole blood sample of a subject
 b. Isolation of the total RNA from said whole blood sample
 c. Determining an expression profile of a set comprising at least one platelet-miRNA from the total RNA isolated
 d. Comparing said expression profile to a reference
 e. Identifying if said subject is affected by progression of AD
 f. Optionally administering said affected subject to therapy (suitable for AD)

In a further preferred embodiment, the expression profile is determined not directly from a whole blood sample, but from a platelet-comprising fraction of said whole blood sample, that is derived from said whole blood sample. Hence from the mixture of white blood cells, red blood cells and platelets the platelet-comprising fraction is prepared by isolation of the platelet fraction or by depletion or removal of the white blood cells and/or the red blood cells from said whole blood sample, hence the expression profile is determined not front of a background of white blood cells and red blood cells. The platelet-comprising fraction may be isolated from said whole blood sample by convenient means (e.g. by centrifugation, size selection) or it may be obtained by depletion or removal of the white blood cells and/or the red blood cells from said whole blood sample using convenient means (e.g. by centrifugation, size selection, differential cell lysis) In that respect, the method of the third aspect of the present invention for monitoring the progression of Alzheimer's Disease comprises the following steps:
 a. Providing a whole blood sample of a subject
 b. Depletion or removal of the white blood cells and/or the red blood cells from the whole blood sample
 c. Isolation of the total RNA from the sample of step b.
 d. Determining an expression profile of a set comprising at least one platelet-miRNA from the total RNA isolated
 e. Comparing said expression profile to a reference
 f. Identifying if said subject is affected by progression of AD
 g. Optionally administering said affected subject to therapy (suitable for AD)

In a fourth aspect, the invention relates to a method for determining the platelet activity in a subject affected by Alzheimer's Disease by determining an expression profile of a set comprising at least one platelet-miRNA from a whole blood sample of a subject wherein the expression profile is determined from a platelet-comprising fraction derived from said whole blood sample.

It is preferred that in said method the set comprising at least one platelet-miRNA is selected from the group consisting of SEQ ID NO: 1 to 20.

It is preferred that the platelet-comprising fraction derived from the whole blood sample is obtained with or without prior depletion or removal of the white blood cells and/or the red blood cells. It is further preferred that the platelet-comprising fraction derived from the whole blood sample is obtained with or without prior isolation of the platelets from the whole blood. It is further preferred that the expression profile of set comprising at least one platelet-miRNA is determined in front or not in front of a background of white blood cells and/or red blood cells.

In a preferred embodiment, the platelet activity of a subject affected (or suspected to be affected) by Alzheimer's Disease may be determined by determining an expression profile of a set comprising at least one platelet-miRNA selected from the group comprising SEQ ID NO: 1 to 20. It is preferred that a pathological platelet activity, hence a platelet activity that is below or above a (pathological) platelet activity threshold may be determined by determining an expression profile of a set comprising at least one platelet-miRNA selected from the group comprising SEQ ID NO: 1 to 20 from a platelet-comprising fraction derived from said whole blood sample. Hence, a subject with a pathological platelet activity may be identified from comparison of said expression profile of a set comprising at least one platelet-miRNA selected from the group comprising SEQ ID NO: 1 to 20 to a reference. Herein, the reference may be a reference expression profile derived from reference subjects with known platelet activity, preferably from subjects with known platelet activity below or above a pathological threshold.

It is preferred that the whole blood sample is collected in a whole blood collection tube, preferably it is collected in a EDTA-, Na-citrate-, ACD- or a Paxgene-like tube, particularly preferred it is collected in a PAXgene™ Blood RNA tube.

In a preferred embodiment, the expression profile is determined directly from a whole blood sample. Hence the mixture of white blood cells, red blood cells and platelets represents the platelet-comprising fraction derived from said whole blood sample. Thus, the expression profile is directly determined from the total RNA isolated from the whole blood sample without prior depletion or removal of the white blood cells and/or the red blood cells or the expression profile is determined directly from the total RNA isolated from the whole blood sample in front of a background of white blood cells and red blood cells or the expression profile is determined directly from the total RNA isolated from the whole blood sample without prior isolation (or extraction) of the platelet fraction. In that respect, the method of the fourth aspect of the present invention for determining the platelet activity in a subject affected with (or suspected to be affected with) Alzheimer's Disease comprises the following steps:
   a. Providing a whole blood sample of a subject
   b. Isolation of the total RNA from said whole blood sample
   c. Determining an expression profile of a set comprising at least one platelet-miRNA from the total RNA isolated
   d. Comparing said expression profile to a reference
   e. Identifying if said subject is affected by a pathological platelet activity
   f. Optionally administering said affected subject to therapy (suitable for AD)

In a further preferred embodiment, the expression profile is determined not directly from a whole blood sample, but from a platelet-comprising fraction of said whole blood sample, that is derived from said whole blood sample. Hence from the mixture of white blood cells, red blood cells and platelets the platelet-comprising fraction is prepared by isolation of the platelet fraction or by depletion or removal of the white blood cells and/or the red blood cells from said whole blood sample, hence the expression profile is determined not front of a background of white blood cells and red blood cells. The platelet-comprising fraction may be isolated from said whole blood sample by convenient means (e.g. by centrifugation, size selection) or it may be obtained by depletion or removal of the white blood cells and/or the red blood cells from said whole blood sample using convenient means (e.g. by centrifugation, size selection, differential cell lysis) In that respect, the method of the fourth aspect of the present invention for determining the platelet activity in a subject affected with (or suspected to be affected with) Alzheimer's Disease comprises the following steps:
   a. Providing a whole blood sample of a subject
   b. Depletion or removal of the white blood cells and/or the red blood cells from the whole blood sample
   c. Isolation of the total RNA from the sample of step b.
   d. Determining an expression profile of a set comprising at least one platelet-miRNA from the total RNA isolated
   e. Comparing said expression profile to a reference
   f. Identifying if said subject is affected by a pathological platelet activity
   g. Optionally administering said affected subject to therapy (suitable for AD)

In a fifth aspect, the invention relates to a method for monitoring the efficacy of an anti-platelet therapy in a subject affected by Alzheimer's Disease by determining an expression profile of a set comprising at least one platelet-miRNA from a whole blood sample of a subject, wherein the expression profile is determined from a platelet-comprising fraction derived from said whole blood sample.

It is preferred that in said method the set comprising at least one platelet-miRNA is selected from the group consisting of SEQ ID NO: 1 to 20.

It is preferred that the platelet-comprising fraction derived from the whole blood sample is obtained with or without prior depletion or removal of the white blood cells and/or the red blood cells. It is further preferred that the platelet-comprising fraction derived from the whole blood sample is obtained with or without prior isolation of the platelets from the whole blood. It is further preferred that the expression profile of set comprising at least one platelet-miRNA is determined in front or not in front of a background of white blood cells and/or red blood cells.

In a preferred embodiment, the efficacy of an anti-platelet therapy of a subject affected (or suspected to be affected) with Alzheimer's Disease may be monitored by determining an expression profile of a set comprising at least one platelet-miRNA selected from the group comprising SEQ ID NO: 1 to 20. It is preferred that a pathological efficacy of an anti-platelet therapy, hence an efficacy of an anti-platelet therapy that is below or above a (pathological) efficacy threshold may be monitored by determining an expression profile of a set comprising at least one platelet-miRNA selected from the group comprising SEQ ID NO: 1 to 20 from a platelet-comprising fraction derived from said whole blood sample. Hence, a subject with a pathological efficacy of an anti-platelet therapy may be identified from comparison of said expression profile of a set comprising at least one platelet-miRNA selected from the group comprising SEQ ID NO: 1 to 20 to a reference. Herein, the reference may be a reference expression profile derived from reference subjects with known efficacy of an anti-platelet therapy, preferably from subjects with known efficacy of an anti-platelet therapy below or above a pathological threshold.

It is preferred that the whole blood sample is collected in a whole blood collection tube, preferably it is collected in a EDTA-, Na-citrate-, ACD- or a Paxgene-like tube, particularly preferred it is collected in a PAXgene™ Blood RNA tube.

In a preferred embodiment, the expression profile is determined directly from a whole blood sample. Hence the mixture of white blood cells, red blood cells and platelets represents the platelet-comprising fraction derived from said whole blood sample. Thus, the expression profile is directly determined from the total RNA isolated from the whole blood sample without prior depletion or removal of the white blood cells and/or the red blood cells or the expression profile is determined directly from the total RNA isolated from the whole blood sample in front of a background of white blood cells and red blood cells or the expression profile is determined directly from the total RNA isolated from the whole blood sample without prior isolation (or extraction) of the platelet fraction. In that respect, the method of the fifth aspect of the present invention for monitoring the efficacy of an anti-platelet therapy in a subject affected with (or suspected to be affected with) Alzheimer's Disease comprises the following steps:
   a. Providing a whole blood sample of a subject
   b. Isolation of the total RNA from said whole blood sample
   c. Determining an expression profile of a set comprising at least one platelet-miRNA from the total RNA isolated
   d. Comparing said expression profile to a reference
   e. Identifying if said subject is affected by a pathological efficacy of an anti-platelet therapy
   f. Optionally administering said affected subject to therapy suitable for AD In a further preferred embodiment, the expression profile is determined not directly from a whole blood sample, but from a platelet-comprising fraction of said whole blood sample, that is derived from said whole blood sample. Hence from the mixture of white blood cells, red blood cells and platelets the platelet-comprising fraction is prepared by isolation of the platelet fraction or by depletion or removal of the white blood cells and/or the red blood cells from said whole blood sample, hence the expression profile is determined not front of a background of white blood cells and red blood cells. The platelet-comprising fraction may be isolated from said whole blood sample by convenient means (e.g. by centrifugation, size selection) or it may be obtained by depletion or removal of the white blood cells and/or the red blood cells from said whole blood sample using convenient means (e.g. by centrifugation, size selection, differential cell lysis) In that respect, the method of the fifth aspect of the present invention for monitoring the efficacy of an anti-platelet therapy in a subject affected with (or suspected to be affected with) Alzheimer's Disease comprises the following steps:
  a. Providing a whole blood sample of a subject
  b. Depletion or removal of the white blood cells and/or the red blood cells from the whole blood sample
  c. Isolation of the total RNA from the sample of step b.
  d. Determining an expression profile of a set comprising at least one platelet-miRNA from the total RNA isolated
  e. Comparing said expression profile to a reference
  f. Identifying if said subject is affected by a pathological efficacy of an anti-platelet therapy
  g. Optionally administering said affected subject to therapy (suitable for AD)

In a further embodiment the determining of an expression profile of a set comprising at least one platelet-miRNA (selected from SEQ ID NO: 1 to 20) from the total RNA isolated according to the first aspect (diagnosing a platelet-related component of AD), second aspect (diagnosing AD), third aspect (monitoring the progression of AD), fourth aspect (determining the platelet activity in AD) or fifth aspect (monitoring the efficacy of an anti-platelet-therapy in AD) of the invention comprises the steps:
  (a) reverse-transcribing the at least one platelet-miRNA comprised in the total RNA isolated (from a whole blood sample or from whole blood sample from which white blood cells and/or red blood cells have been depleted or removed or from whole blood sample from which white blood cells and/or red blood cells have been not depleted or not removed) into non-naturally occurring cDNA
  (b) optionally amplifying the cDNA of step (a)
  (c) quantifying the optionally amplified cDNA, thereby determining the expression profile of said miRNAs Herein it is preferred that miRNA-specific or universal reverse transcription DNA-primers are used for reverse transcription in step (a). Examples of miRNA-specific reverse transcription primers are listed in column B of FIG. 3, examples of universal reverse transcription primers are Oligo-d(T)-Primers or RT primers listed in column C of FIG. 6. It is further preferred that miRNA-specific forward primer and universal reverse primer or alternatively universal forward and universal reverse primer are used for optionally amplifying the cDNA in step (b). Examples of miRNA-specific forward primer and universal reverse primer are listed in column C and D of FIG. 3, examples of universal forward and universal reverse primer are listed in column D and E of FIG. 6. Further, it is preferred that miRNA-specific forward primer and universal reverse primer or alternatively miRNA-specific forward and partially universal reverse primer are used for quantifying the optionally amplified cDNA in step (c). It is preferred that the quantifying in step (c) is performed by real-time PCR, nucleic acid hybridization (e.g. microarray) or sequencing (e.g. next generation sequencing) techniques. It is preferred that the quantifying in step (c) by real-time PCR is utilizing dual-labeled hydrolysis probes that make use of the 5'-3' exonuclease activity of polymerase (e.g. Taqman-probes) or DNA-intercalating dyes (e.g. SYBRgreen). Examples of miRNA-specific forward primer and universal reverse primer are listed in column C and D of FIG. 3, examples of miRNA-specific forward and partially universal reverse primer are listed in column B and C of FIG. 4; examples of dual-labeled hydrolysis probes are listed in column E of FIG. 3.

In a still further embodiment the determining of an expression profile of a set comprising at least one platelet-miRNA (selected from SEQ ID NO: 1 to 20) from the total RNA isolated according to the first aspect (diagnosing a platelet-related component of AD), second aspect (diagnosing AD), third aspect (monitoring the progression of AD), fourth aspect (determining the platelet activity in AD) or fifth aspect (monitoring the efficacy of an anti-platelet-therapy in AD) of the invention comprises the steps:
  (a) adding a DNA-fragment to the 3'-end of the at least one platelet-miRNA comprised in the total RNA isolated (from a whole blood sample or from whole blood sample from which white blood cells and/or red blood cells have been depleted or removed or from whole blood sample from which white blood cells and/or red blood cells have been not depleted or not removed), thereby forming non-naturally occurring RNA-DNA hybrids
  (b) optionally reverse-transcribing said RNA-DNA hybrids to cDNA
  (c) quantifying the optionally reverse-transcribed RNA-DNA hybrids, thereby determining the expression profile of said miRNAs Herein it is preferred that DNA-fragments of 1 to 150 nucleotides in length (preferably of 1 to 100 nt, more preferably of 1 to 50 nt, even more preferably of 1 to 30 nt in length) are added in step (a) to the 3'-end of the miRNAs by ligation or by polymerase-based elongation. Examples of said DNA-fragments are listed in FIG. 5 or column A of FIG. 6.

It is preferred that (miRNA-specific or) universal reverse transcription DNA-primers are used for reverse transcription in step (b). Further, it is preferred that miRNA-specific forward primer and universal reverse primer or alternatively miRNA-specific forward and partially universal reverse primer are used for quantifying the optionally amplified cDNA in step (c). Examples of miRNA-specific reverse transcription primers are listed in column B of FIG. 3, examples of universal reverse transcription primers are oligo-d(T)-Primers or RT primers listed in column C of FIG. 6. It is preferred that the quantifying in step (c) is performed by real-time PCR, nucleic acid hybridization or sequencing (e.g. next generation sequencing) techniques. It is preferred that the quantifying in step (c) by real-time PCR is utilizing dual-labeled hydrolysis probes that make use of the 5'-3' exonuclease activity of polymerase (e.g. Taqman-probes) or DNA-intercalating dyes (e.g. SYBRgreen).

In a still further embodiment the determining of an expression profile of a set comprising at least one platelet-miRNA (selected from SEQ ID NO: 1 to 20) from the total RNA isolated according to the first aspect (diagnosing a platelet-related component of AD), second aspect (diagnosing AD), third aspect (monitoring the progression of AD), fourth aspect (determining the platelet activity in AD) or fifth aspect (monitoring the efficacy of an anti-platelet-therapy in AD) of the invention comprises the steps:
  (a) adding a RNA-fragment to the 3'-end of the at least one platelet-miRNA comprised in the total RNA isolated (from a whole blood sample or from whole blood sample from which white blood cells and/or red blood cells have been depleted or removed or from whole blood sample from which white blood cells and/or red blood cells have been not depleted or not removed), thereby forming non-naturally occurring RNA-RNA hybrids (b) optionally reverse-transcribing said RNA-RNA hybrids to cDNA (c) quantifying the optionally reverse-transcribed RNA-RNA hybrids, thereby determining the expression profile of said miRNAs Herein it is preferred that RNA-fragments of 1 to 150 nucleotides in length (preferably of 1 to 100 nt, more preferably of 1 to 50 nt, even more preferably of 1 to 30 nt in length) are added in step (a) to the 3'-end of the miRNAs preferably by poly(A)-tailing reaction. The reverse-transcription of step (b) is preferably with universal RT-primers, e.g. oligo-d(T)-primers. The quantifying in step (c) is preferably utilizing miRNA-specific forward and partially universal reverse primer, e.g. miRNA-specific forward and partially universal reverse primer as listed in column B and C of FIG. 4.

In a sixth aspect, the invention relates to a kit for use in the method according to any of the first, second, third, fourth or fifth aspect of the present invention including all of its embodiments.

Said kit for use in the method according to any of the first, second, third, fourth or fifth aspect of the present invention comprises:

a) means for determining an expression profile of a set comprising at least one platelet-miRNA b) a reference derived from at least one reference expression profile c) optionally a data carrier d) optionally means for deriving a platelet-comprising fraction from a whole blood sample e) optionally a whole blood collection tube wherein the expression profile and the reference expression profile are obtained from said at least one platelet-miRNAs selected from the group consisting SEQ ID NO: 1 to 20 and wherein the expression profile and the reference expression profile are determined from a platelet-comprising fraction derived from a whole blood sample (from a subject affected or suspected to be affected by AD).

In a preferred embodiment, the reference may be contained in the data carrier of the kit.

In a further preferred embodiment the kit may contain a reference sample and/or a reference standard that is included in the kit and which is employed when performing the kit, e.g. in the determining of the expression profile.

The kit optionally comprises a data carrier. Preferably the data carrier is an electronic or a non-electronic data carrier, more preferably it is an electronic data carrier, such as a storage medium.

It is preferred that the data carrier comprised in the kit comprises a guide for use of the kit in the method according to any of the first, second, third, fourth or fifth aspect of the present invention. This guide may include instructions for the doctor and/or the diagnostic laboratory that are involved in the method according to any of the first, second, third, fourth or fifth aspect of the present invention. The guide may include a reference according to the present invention.

It is preferred that the data carrier further comprises tools for analysis and evaluation of the determined expression profile(s). These tools may be any tools to assist the doctor and/or the diagnostic laboratory in the method according to any of the first, second, third, fourth or fifth, aspect of the present invention. Preferably, these tools are software-tools that assist in analysis of the determined expression profile(s) and/or assist in the subsequently diagnosis. The tools for analysis and evaluation may include a reference according to the present invention.

The kit optionally comprises optionally means for deriving a platelet-comprising fraction from a whole blood sample. Said means are for preparing said platelet-comprising fraction from said whole blood sample, wherein said means may include means for removal or depletion of white blood cells and/or red blood cells from said whole blood sample (e.g. by centrifugation, by size selection techniques, by differential cell lysis, e.g. by differential red blood cell lysis), means for isolation of platelets from said whole blood sample (e.g. by centrifugation, by size selection techniques).

The kit optionally comprises a whole blood collection tube, which is preferably selected from group consisting of EDTA-, Na-citrate-, ACD-, Heparin-, PAXgene™ Blood RNA-, Tempus Blood RNA-tubes and which optionally may contain an additive for stabilizing the RNA- and/or the miRNA-fraction.

In summary, the present invention is composed of the following items:

1. Method for diagnosing a platelet-related (or platelet-activated) component of Alzheimer's Disease by determining an expression profile of a set comprising at least one platelet-miRNA from a whole blood sample of a subject (affected or suspected to be affected by Alzheimer's Disease), wherein the expression profile is determined from a platelet-comprising fraction derived from said whole blood sample.

2. Method for diagnosing Alzheimer's Disease by determining an expression profile of a set comprising at least one platelet-miRNA from a whole blood sample of a subject (affected or suspected to be affected by Alzheimer's Disease), wherein the expression profile is determined from a platelet-comprising fraction derived from said whole blood sample.

3. Method for monitoring the progression of Alzheimer's Disease in a subject by determining an expression profile of a set comprising at least one platelet-miRNA from a whole blood sample of a subject (affected or suspected to be affected by Alzheimer's Disease), wherein the expression profile is determined from a platelet-comprising fraction derived from said whole blood sample.

4. Method for determining the platelet activity in a subject affected or suspected to be affected by Alzheimer's Disease by determining an expression profile of a set comprising at least one platelet-miRNA from a whole blood sample of a subject wherein the expression profile is determined from a platelet-comprising fraction derived from said whole blood sample.

5. Method for monitoring the efficacy of an anti-platelet therapy in a subject affected or suspected to be affected by Alzheimer's Disease by determining an expression profile of a set comprising at least one platelet-miRNA from a whole blood sample of a subject, wherein the expression profile is determined from a platelet-comprising fraction derived from said whole blood sample.

6. The method according to any of the items 1 to 5, wherein the platelet-miRNAs are selected from the group consisting of SEQ ID NO: 1 to 20.

7. The method according to any of the items 1 to 6, wherein the expression profile is determined from a whole blood sample with or without prior depletion or removal of the white blood cells and/or the red blood cells.

8. The method according to any of the items 1 to 7, comprising the steps:
   a. Providing a whole blood sample of a subject
   b. Isolation of the total RNA from said whole blood sample
   c. Determining an expression profile of a set comprising at least one platelet-miRNA from the total RNA isolated
   d. Comparing said expression profile to a reference
   e. Identifying if said subject is affected by an Alzheimer's Disease related condition as detailed in the method according to any of the items 1 to 5
   f. Optionally administering said affected subject to therapy 9. The method according to item 8, wherein the platelet-comprising fraction is derived from a whole blood sample without prior removal of the white blood cells and/or the red blood cells.

10. The method according to any of the items 1 to 7, comprising the steps:
    a. Providing a whole blood sample of a subject
    b. Depletion or removal of the white blood cells and/or the red blood cells from the whole blood sample
    c. Isolation of the total RNA from the depleted (or removed) sample
    d. Determining an expression profile of a set comprising at least one platelet-miRNA from the total RNA isolated
    e. Comparing said expression profile to a reference
    f. Identifying if said subject is affected by Alzheimer's Disease related condition as detailed in the method according to any of the items 1 to 5
    g. Optionally administering said affected subject to therapy 11. The method according to item 10, wherein the platelet-comprising fraction is platelet-rich-plasma or platelet-concentrate.

12. The method according to any of the items 1 to 11, wherein the whole blood sample is collected in a whole blood collection tube, optionally containing an additive for RNA stabilization, preferably optionally containing an additive for stabilization of intracellular RNA, more preferably the whole blood collection tube is a PAXgene™ Blood RNA tube 13. The method according to item 12 wherein the additive for RNA-stabilization is selected from the group consisting of catrimox-14, tetradecyltrimethylammonium oxalate, RNA-later, RNAsin or RNAretain.

14. A kit for use in the method according to any of the items 1 to 12, comprising:
    a) means for determining an expression profile of a set comprising at least one platelet-miRNA
    b) a reference derived from at least one reference expression profile
    c) optionally a data carrier
    d) optionally means for deriving a platelet-comprising fraction from a whole blood sample
    e) optionally a whole blood collection tube
    wherein the expression profile and the reference expression profile are obtained from said at least one platelet-miRNAs selected from the group consisting SEQ ID NO: 1 to 20 and wherein the expression profile and the reference expression profile are determined from a platelet-comprising fraction derived from a whole blood sample.

15. The kit according to item 14, wherein the whole blood collection tube is a PAXgene™ Blood RNA tube.

16. The method according to any of the items 1 to 13, wherein the determining of an expression profile of a set comprising at least one platelet-miRNA comprises the steps:
    (a) reverse-transcribing the miRNAs comprised in the total RNA isolated (from a whole blood sample or from whole blood sample from which white blood cells and/or red blood cells have been depleted or removed or from whole blood sample from which white blood cells and/or red blood cells have been not depleted or not removed) into non-naturally occurring cDNA
    (b) optionally amplifying the cDNA of step (a)
    (c) quantifying the optionally amplified cDNA, thereby determining the expression profile of said miRNAs 17. The method according to item 16, wherein miRNA-specific or universal reverse transcription DNA-primers are used for reverse transcription in step (a).

18. The method according to any of the items 16 to 17, wherein miRNA-specific forward primer and universal reverse primer or miRNA-specific forward and partially universal reverse primer are used for quantifying the optionally amplified cDNA in step (c).

19. The method according to any of the items 16 to 18, wherein miRNA-specific forward primer and universal reverse primer or miRNA-specific forward and partially universal reverse primer are used for optionally amplifying the cDNA in step (b).

20. The method according to any of the items 16 to 19 wherein that the quantifying in step (c) is performed by real-time PCR, nucleic acid hybridization or sequencing techniques.

21. The method according to any of the items 1 to 13, wherein the determining of an expression profile of a set comprising at least one platelet-miRNA comprises the steps:
    (a) adding a DNA-fragment to the 3'-end of the miRNAs comprised in the total RNA isolated (from a whole blood sample or from whole blood sample from which white blood cells and/or red blood cells have been depleted or removed or from whole blood sample from which white blood cells and/or red blood cells have been not depleted or not removed), thereby forming non-naturally occurring RNA-DNA hybrids
    (b) optionally reverse-transcribing said RNA-DNA hybrids to cDNA
    (c) quantifying the optionally reverse-transcribed RNA-DNA hybrids, thereby determining the expression profile of said miRNAs 22. The method according to item 21, wherein DNA-fragments of 1 to 150 nucleotides in length are added to the 3'-end of the miRNAs by ligation or by polymerase-based elongation.

23. The method according to any of the items 21 to 22, wherein universal reverse transcription DNA-primers are used for reverse transcription in step (b).

24. The method according to any of the items 21 to 23, wherein miRNA-specific forward primer and universal reverse primer or miRNA-specific forward and partially universal reverse primer are used for quantifying the optionally amplified cDNA in step (c).

25. The method according to any of the items 21 to 24, wherein that the quantifying in step (c) is performed by real-time PCR, nucleic acid hybridization or sequencing techniques.

26. The method according to any of the items 8 to 13 or 16 to 25, wherein the administering said affected subject to therapy includes administration of cholinesterase inhibitors for early to moderate stages of AD or memantine to treat the cognitive symptoms for moderate to severe stages of AD.

BRIEF DESCRIPTION OF THE DRAWINGS

FIG. 1: Overview of the platelet-miRNAs (with SEQ ID NO: 1 to 20) well suited in the method, use or kit for diagnosing a platelet-related or platelet-activated component of AD, for diagnosing AD, for monitoring the progression of AD, for determining the platelet-activity in AD and/or for monitoring the efficacy of anti-platelet therapy in AD and for determining an expression profile according to the present invention. With "SEQ ID NO:"=sequence identification number, "miRNA"=identifier of the miRNA according to miRBase (www.mirbase.org), "Sequence"=(5'-3')-sequence of the miRNA.

FIG. 2: ALZHEIMER'S DISEASE (AD): Platelet-miRNAs well suited in the method, use or kit for diagnosing a platelet-related or platelet-activated component of AD, for diagnosing AD, for monitoring the progression of AD, for determining the platelet-activity in AD and/or for monitoring the efficacy of anti-platelet therapy in AD and for determining an expression profile according to the present invention. With "SEQ ID NO:"=sequence identification number, "miRNA"=identifier of the miRNA according to miRBase (www.mirbase.org), "Healthy Control median g1"=median intensity (expression level) obtained from microarray analysis for healthy control subjects in counts/sec; "Alzheimer's Disease median g2"="=median intensity (expression level) obtained from microarray analysis for Alzheimer's Disease subjects in counts/sec; "Fold Change (g1/g2)"=expression fold-change by calculating the ration of the values g1/g2 from "Healthy Control median g1" and "Alzheimer's Disease median g2"; "ttest adjpval"=adjusted p-value obtained when applying t-test and reducing false-discovery rate by applying Benjamini-Hochberg-adjustment; "limma adjpval"=adjusted p-value obtained when applying limma-test and reducing false-discovery rate by applying Benjamini-Hochberg-adjustment; "AUC"=area under the curve-value of ROC-curve statistical model.

FIG. 3: miRNA-specific DNA-primers (column B) used for reverse transcription (RT) of at least one platelet-miRNA with SEQ ID NO: 1 to 20 to non-naturally occurring cDNA; miRNA-specific forward and universal reverse primers (column C, D) for quantification and optionally amplification of at least one platelet-miRNA with SEQ ID NO: 1 to 20 employed for determining of an expression profile of a set comprising at least one platelet-miRNA representative for AD; dual-labeled hydrolysis probes (Taqman-probes, column E)) utilized for quantifying of at least one platelet-miRNA with SEQ ID NO: 1 to 20 by real-time PCR.

FIG. 4: miRNA-specific forward primer (column B) and partially universal reverse primer (column C) for quantification and optionally amplification of cDNA-transcripts at least one platelet-miRNA with SEQ ID NO: 1 to 20 employed for determining of an expression profile of a set comprising at least one platelet-miRNA representative for AD.

FIG. 5: DNA-fragments added to the 3'-end of the at least one platelet-miRNA with SEQ ID NO: 1 to 20 employed for determining of an expression profile of a set comprising at at least one platelet-miRNA representative for AD, thereby forming non-naturally occurring RNA-DNA hybrids.

FIG. 6: Adapters, RT-primers and PCR-primers utilized for next generation sequencing (Illumina small RNA-seq) of the miRNAs with SEQ ID NO: 1 to 20 employed for determining of an expression profile of a set comprising at least one platelet-miRNA representative for AD: universal 3' RNA Adapters (column A) ligated to the 3'-end of the at least one platelet-miRNA with SEQ ID NO: 1 to 20; universal 5' RNA Adapter (column B) ligated to the 5'-end of the miRNAs with SEQ ID NO: 1 to 20; universal reverse transcription (RT)-Primers (column C) for reverse-transcribing the 3'- and 5'-adapter ligated miRNAs into (non-naturally occurring) cDNA; Small RNA PCR Primer 1=universal forward (column D) and Small RNA PCR Primer 2=universal reverse (PCR) primers (column E) for amplifying the 3'- and 5'-adapter ligated and reverse-transcribed cDNAs of the at least one platelet-miRNA with SEQ ID NO: 1 to 20.

EXAMPLES

The Examples are designed in order to further illustrate the present invention and serve a better understanding. They are not to be construed as limiting the scope of the invention in any way.

Example 1

Preparation of Total RNA for Determination of Platelet-miRNAs from Whole Blood Samples without Prior Depletion or Removal of the White Blood Cells and/or the Red Blood Cells Blood of AD-patients and healthy controls was drawn by venipuncture in PAXgene™ Blood RNA tubes (PreAnalytiX GmbH, Hombrechtikon, Switzerland). The tubes were gently inverted 10-15 times. For each blood donor, 2.5 ml of peripheral whole blood was collected. Herein, the blood cell pellet (the intra-cellular blood fraction comprising red blood cells, white blood cells and platelets) was collected at the bottom of the tube by centrifugation. For further processing the blood cell pellet was used, while the supernatant (including the extra-cellular blood fraction) was discarded. Total RNA, including the small RNA (miRNA-fraction) was isolated from the pelleted blood cells using the miRNeasy Mini Kit (Qiagen GmbH, Hilden, Germany) and the resulting RNA were stored at −80° C. before use in expression profiling experiments.

Example 2

Next Generation Sequencing-Based Determination of Expression Profiles

The Alzheimer's Disease (AD) data is based on next generation sequencing data of Leidinger P. et.al., (Genome Biol. 2013 29; 14(7):R78), wherein the AD raw data was extracted from GEO database (GSE46579), subjected to a quantile normalization scheme, before the resulting data underwent the statistical analysis and data filtering detailed in Example 3 and Example 4.

Example 3

Statistical Analysis

After having verified the normal distribution of the measured AD data, a parametric t-test (unpaired, two-tailed) was carried out for each miRNA separately, to detect miRNAs that show a different behavior in different groups of blood donors. The resulting p-values were adjusted for multiple testing by Benjamini-Hochberg adjustment (=ttestadjpval). Furthermore, we applied the limma-test for each miRNA separately and corrected according to Benjamini-Hochberg (=limma_adjpval). Additionally, we applied receiver operating characteristics and calculated the "Area under the Curve"-value (=AUC). The ttest-, limma-test- and AUC-values allow to judge on the statistical significance for each miRNA to be differential expressed between group 1 (g1=Healthy Control subjects) and group 2 (g2=AD subjects).

Example 4

Data Filtering

The AD quantile normalized dataset (Healthy Control vs. Alzheimer's Disease subjects) was subjected to strict filtering rules in order identify the platelet-miRNAs with SEQ IDNO: 1 to 20, that are employed in the determination of expression profiles in a platelet-comprising fraction derived from the whole blood sample starting from whole blood collected in a PAXgene™ Blood RNA tube without prior depletion or removal of white blood cells and/or red blood cells (or without prior isolation of the platelet fraction or in front of a background of white blood cells and/or red blood cells), which may e.g. be employed as biomarkers for non-invasive diagnosis of AD, for non-invasive diagnosis of a platelet-related (platelet-activated) component of AD, or. may be employed as biomarkers for determining the platelet-activity in AD and/or for monitoring the efficacy of anti-platelet therapy in AD.

From the AD quantile normalized dataset all miRNAs were discarded that had (1) a median intensity g1 or g2 (expression level) below 100 reads or (2) an expression fold change ratio g1/g2 in between 0.66 and 1.5 (translating to low differential expression with a threshold below 1.5-fold). By manual curating of the data one exception to this filtering scheme a was tolerated (hsa-miR-221-3p, when the g2 (AD) expression level was below the 100 read threshold, but the g1 (Healthy Control) showed strong up-regulation.

Next, the remaining miRNA-biomarker candidates were aligned to a list of selected platelet-miRNAs described to be highly expressed in platelets (PMID 21415270, 22371016, 23323973), wherein the list of highly expressed miRNAs contained the 30% highest expressed platelet-miRNAs.

Example 5

Patient Characteristics

| FIG. | Group g1 = Control | No. Control Subjects | Group g2 = Disease | No. Disease Subjects |
|---|---|---|---|---|
| 2 | Healthy Control | 22 | Alzheimer's Disease | 48 |

Example 6

Preparation of Platelet-Comprising Fraction of a Whole Blood Sample with Prior Depletion or Removal of White Blood Cells and/or Red Blood Cells Platelet-comprising fractions include, but are not limited to, platelet-rich-plasma (PRP), Leukocyte-depleted platelet-rich-plasma, platelet-concentrate or Leukocyte-depleted platelet concentrate.

5.1 Blood Draw

For platelet-preparations derived from whole blood, venous blood is conveniently drawn into EDTA-tubes (7.5 ml S-Monovette, Sarstedt/10 ml, Vaccutainer, BD Heidelberg, Germany), Na-citrate tubes (380%; 4.5 ml Vaccutainer, BD Heidelberg, Germany) or ACD-tubes (ACD type A, 8.5 ml, ACD type B, 6.5 ml Vaccutainer, BD Heidelberg, Germany).

5.2 Preparation of Platelet-Rich-Plasma (PRP)

Freshly collected whole blood is centrifuged with soft spin (170 g, 15 min) to make Platelet-Rich-Plasma (PRP), buffy coat (white blood cells) and red blood cells, from which the PRP is collected.

Leukocyte-depleted PRP is obtained by either filtering the collected PRP through leukocyte depletion filters (Pall corporation, Port Washington, N.Y., ISA) or by negative selection employing magnetic cell sorting using human CD45+ magnetic beads (Miltenyi Biotech, Bergisch Gladbach, Germany).

Platelet-concentrate is obtained from PRP by a second hard spin centrifugation (5000 g, 3 min), where platelets are pelleted out of the plasma to yield platelet-concentrate and platelet-poor-plasma (PPP).

5.3 Preparation of Platelet-Concentrate from Buffy Coat

The collected whole blood is centrifuged with hard spin (5000 g, 7 min) to make Platelet-Poor-Plasma (PPP), buffy coat (including white blood cells & platelets) and red blood cells, from which the buffy coat comprising the platelets is collected. To concentrate the platelets, the buffy coat is further centrifuged (2000 g, 3 min).

Leukocyte-depleted platelet concentrate is obtained by either filtering through leukocyte depletion filters (Pall corporation, Port Washington, N.Y., ISA) or by negative selection employing magnetic cell sorting using human CD45+ magnetic beads (Miltenyi Biotech, Bergisch Gladbach, Germany).

The invention claimed is:

1. A method for monitoring the progression of Alzheimer's disease in a subject or efficacy of an anti-platelet therapy in a subject affected by Alzheimer's disease, comprising determining an expression profile of a set comprising at least one miRNA in platelet-rich plasma of a subject, and administering an Alzheimer's disease therapy to the subject wherein the at least one miRNA is selected from the group consisting of SEQ ID NOs:1, 2, 4-7, 9, 11 and 13-20, and wherein the platelet-rich plasma does not comprise white blood cells.

2. A method for determining the platelet activity in a subject affected by Alzheimer's disease, comprising determining an expression profile of a set comprising at least one miRNA in platelet-rich plasma of a subject, and administering an Alzheimer's disease therapy to the subject wherein the at least one miRNA is selected from the group consisting of SEQ ID NOs:1, 2, 4-7, 9, 11 and 13-20, and wherein the platelet-rich plasma does not comprise white blood cells.

3. The method of claim 1, further comprising the steps of:
   (a) providing platelet-rich plasma of a subject;
   (b) isolating total RNA from the sample provided in (a);
   (c) determining an expression profile of a set comprising at least one platelet-miRNA from the total RNA isolated;
   (d) comparing said expression profile to a reference;
   (e) identifying whether the subject is affected by a platelet-related component of Alzheimer's disease; and administering an Alzheimer's disease therapy to the subject.

4. The method of claim 1, further comprising the steps of:
   (a) removing white blood cells and optionally red blood cells from a whole blood sample, thereby providing platelet-rich plasma;
   (b) isolating total RNA from the sample provided in (a);
   (c) determining an expression profile of a set comprising at least one platelet-miRNA from the total RNA isolated;
   (d) comparing said expression profile to a reference;
   (e) identifying whether said subject is affected by a platelet-related component of Alzheimer's disease, and
   (f) administering an Alzheimer's disease therapy to said subject.

5. The method of claim 1, wherein the determining of an expression profile of a set comprising at least one miRNA comprises the steps of:
   (a) reverse-transcribing the at least one miRNA into non-naturally occurring cDNA;
   (b) optionally amplifying the cDNA of step (a); and
   (c) quantifying the optionally amplified cDNA, thereby determining the expression profile of said at least one miRNA.

6. The method of claim 1, wherein the determining of an expression profile of a set comprising at least one miRNA comprises the steps of:
   (a) adding a DNA-fragment to the 3'-end of the at least one miRNA, thereby forming a non-naturally occurring RNA-DNA hybrid;
   (b) optionally reverse-transcribing said RNA-DNA hybrid to cDNA; and
   (c) quantifying the optionally reverse-transcribed RNA-DNA hybrid, thereby determining the expression profile of said at least one miRNA.

7. The method of claim 3, wherein the administering an Alzheimer's disease therapy to the affected subject includes administration of cholinesterase inhibitors for early to moderate stages of AD or memantine to treat the cognitive symptoms for moderate to severe stages of AD.

8. The method of claim 2, further comprising the steps of:
(a) providing platelet-rich plasma of a subject;
(b) isolating total RNA from the sample provided in (a);
(c) determining an expression profile of a set comprising at least one platelet-miRNA from the total RNA isolated;
(d) comparing said expression profile to a reference;
(e) identifying if said subject is affected by a platelet-related component of Alzheimer's disease; and
(f) administering an Alzheimer's disease therapy to said subject.

9. The method of claim 2, further comprising the steps of:
(a) removing white blood cells and optionally red blood cells from a whole blood sample, thereby providing platelet-rich plasma;
(b) isolating total RNA from the sample provided in (a),
(c) determining an expression profile of a set comprising at least one platelet-miRNA from the total RNA isolated;
(d) comparing said expression profile to a reference;
(e) identifying whether the subject is affected by a platelet-related component of Alzheimer's disease; and
(f) administering an Alzheimer's disease therapy to said subject.

10. The method of claim 2, wherein the determining of an expression profile of a set comprising at least one miRNA comprises the steps of:
(a) reverse-transcribing the at least one miRNA into non-naturally occurring cDNA;
(b) optionally amplifying the cDNA of step (a); and
(c) quantifying the optionally amplified cDNA, thereby determining the expression profile of said at least one miRNA.

11. The method of claim 2, wherein the determining of an expression profile of a set comprising at least one miRNA comprises the steps of:
(a) adding a DNA-fragment to the 3'-end of the at least one miRNA, thereby forming a non-naturally occurring RNA-DNA hybrid;
(b) optionally reverse-transcribing said RNA-DNA hybrid to cDNA; and
(c) quantifying the optionally reverse-transcribed RNA-DNA hybrid, thereby determining the expression profile of said at least one miRNA.

12. The method of claim 8, wherein the administering an Alzheimer's disease therapy to said affected subject includes administration of cholinesterase inhibitors for early to moderate stages of AD or memantine to treat the cognitive symptoms for moderate to severe stages of AD.

* * * * *

SEQUENCE LISTING

<160> NUMBER OF SEQ ID NOS: 20

<210> SEQ ID NO 1
<211> LENGTH: 23
<212> TYPE: RNA
<213> ORGANISM: Homo sapiens

```
<400> SEQUENCE: 1
uguaaacauc cuacacucuc agc                                          23

<210> SEQ ID NO 2
<211> LENGTH: 23
<212> TYPE: RNA
<213> ORGANISM: Homo sapiens

<400> SEQUENCE: 2
aaugacacga ucacucccgu uga                                          23

<210> SEQ ID NO 3
<211> LENGTH: 21
<212> TYPE: RNA
<213> ORGANISM: Homo sapiens

<400> SEQUENCE: 3
cuagacugaa gcuccuugag g                                            21

<210> SEQ ID NO 4
<211> LENGTH: 22
<212> TYPE: RNA
<213> ORGANISM: Homo sapiens

<400> SEQUENCE: 4
uguaaacauc cccgacugga ag                                           22

<210> SEQ ID NO 5
<211> LENGTH: 22
<212> TYPE: RNA
<213> ORGANISM: Homo sapiens

<400> SEQUENCE: 5
caaagaauuc uccuuuuggg cu                                           22

<210> SEQ ID NO 6
<211> LENGTH: 24
<212> TYPE: RNA
<213> ORGANISM: Homo sapiens

<400> SEQUENCE: 6
ucccugagac ccuuuaaccu guga                                         24

<210> SEQ ID NO 7
<211> LENGTH: 23
<212> TYPE: RNA
<213> ORGANISM: Homo sapiens

<400> SEQUENCE: 7
caacggaauc ccaaaagcag cug                                          23

<210> SEQ ID NO 8
<211> LENGTH: 22
<212> TYPE: RNA
<213> ORGANISM: Homo sapiens

<400> SEQUENCE: 8
ugagguagua gauuguauag uu                                           22

<210> SEQ ID NO 9
<211> LENGTH: 22
<212> TYPE: RNA
```

```
<213> ORGANISM: Homo sapiens

<400> SEQUENCE: 9
uggagagaaa ggcaguuccu ga                                          22

<210> SEQ ID NO 10
<211> LENGTH: 23
<212> TYPE: RNA
<213> ORGANISM: Homo sapiens

<400> SEQUENCE: 10
agcagcauug uacagggcua uga                                         23

<210> SEQ ID NO 11
<211> LENGTH: 22
<212> TYPE: RNA
<213> ORGANISM: Homo sapiens

<400> SEQUENCE: 11
ugagguagua gguuguauag uu                                          22

<210> SEQ ID NO 12
<211> LENGTH: 23
<212> TYPE: RNA
<213> ORGANISM: Homo sapiens

<400> SEQUENCE: 12
agcagcauug uacagggcua uca                                         23

<210> SEQ ID NO 13
<211> LENGTH: 22
<212> TYPE: RNA
<213> ORGANISM: Homo sapiens

<400> SEQUENCE: 13
ucagugcauc acagaacuuu gu                                          22

<210> SEQ ID NO 14
<211> LENGTH: 22
<212> TYPE: RNA
<213> ORGANISM: Homo sapiens

<400> SEQUENCE: 14
ugagguagua aguuguauug uu                                          22

<210> SEQ ID NO 15
<211> LENGTH: 22
<212> TYPE: RNA
<213> ORGANISM: Homo sapiens

<400> SEQUENCE: 15
ugagguagua guuuguacag uu                                          22

<210> SEQ ID NO 16
<211> LENGTH: 22
<212> TYPE: RNA
<213> ORGANISM: Homo sapiens

<400> SEQUENCE: 16
uagcagcaca uaaugguuug ug                                          22

<210> SEQ ID NO 17
<211> LENGTH: 22
```

```
<212> TYPE: RNA
<213> ORGANISM: Homo sapiens

<400> SEQUENCE: 17
aaaccguuac cauuacugag uu                                                22

<210> SEQ ID NO 18
<211> LENGTH: 23
<212> TYPE: RNA
<213> ORGANISM: Homo sapiens

<400> SEQUENCE: 18
agcuacauug ucugcugggu uuc                                               23

<210> SEQ ID NO 19
<211> LENGTH: 22
<212> TYPE: RNA
<213> ORGANISM: Homo sapiens

<400> SEQUENCE: 19
uagcuuauca gacugauguu ga                                                22

<210> SEQ ID NO 20
<211> LENGTH: 21
<212> TYPE: RNA
<213> ORGANISM: Homo sapiens

<400> SEQUENCE: 20
cauuauuacu uuugguacgc g                                                 21
```